(12) United States Patent
Denny et al.

(10) Patent No.: US 7,816,521 B2
(45) Date of Patent: Oct. 19, 2010

(54) 1,2,4-BENZOTRIAZINE-1,4-DIOXIDES

(75) Inventors: William Alexander Denny, Auckland (NZ); Michael Patrick Hay, Auckland (NZ); Kevin Owen Hicks, Auckland (NZ); Frederik Pruijn, Auckland (NZ); William Robert Wilson, Waiuku (NZ); Karin Pchalek, Auckland (NZ)

(73) Assignee: Auckland Uniservices Limited, Auckland (NZ)

( * ) Notice: Subject to any disclaimer, the term of this patent is extended or adjusted under 35 U.S.C. 154(b) by 979 days.

(21) Appl. No.: 10/590,796

(22) PCT Filed: Mar. 1, 2005

(86) PCT No.: PCT/NZ2005/000034
§ 371 (c)(1),
(2), (4) Date: Nov. 2, 2006

(87) PCT Pub. No.: WO2005/082867
PCT Pub. Date: Sep. 9, 2005

(65) Prior Publication Data
US 2007/0197534 A1    Aug. 23, 2007

(30) Foreign Application Priority Data
Mar. 1, 2004    (NZ) ..................... 531499

(51) Int. Cl.
C07D 253/10    (2006.01)
C07D 413/12    (2006.01)
A61K 31/53    (2006.01)
A61P 35/00    (2006.01)

(52) U.S. Cl. ............... 544/183; 514/243; 514/231.5; 544/112

(58) Field of Classification Search ........... 544/183, 544/112; 514/243, 231.5
See application file for complete search history.

(56) References Cited

U.S. PATENT DOCUMENTS

| | | | |
|---|---|---|---|
| 3,991,189 A | 11/1976 | Seng et al. | |
| 4,027,022 A | 5/1977 | Seng et al. | |
| 5,175,287 A | 12/1992 | Lee et al. | |
| 2002/0103200 A1 | 8/2002 | Lee et al. | |

FOREIGN PATENT DOCUMENTS

| | | |
|---|---|---|
| AU | 2003265023 A1 | 4/2004 |
| DE | 272 591 A1 | 10/1989 |
| EP | 0 649 658 A1 | 4/1995 |
| WO | WO 89/08647 | 9/1989 |
| WO | WO 91/04028 | 4/1991 |
| WO | WO 97/11699 | 4/1997 |
| WO | WO 2004/026846 A1 | 4/2004 |

OTHER PUBLICATIONS

Bussink et al., Radiotherapy and Oncology, 67, 3-15, 2003.*
Cecil Textbook of Medicine, edited by Bennet, J.C., and Plum F., 20th edition, vol. 1, 1004-1010, 1996.*
Freshney et al., Culture of Animal Cells, A Manual of Basic Technique, Alan R. Liss, Inc., 1983, New York, p. 4.*
Dermer et al., Bio/Technology, 1994, 12:320.*
Cohen et al., Current Opinion in Chemical Biology, 3,459-465, 1999.*
Golub et al., Science, 286, 531-537, 1999.*
CA 138:304247 & Tetrahedron Letters, 2002, vol. 43(52, pp. 9569-9571, M.P. Hay et al; "New and Versatile Synthesis of 3-alkyl- and 3-aryl-1,2,4-benzotriazine 1,4-dioxides: preparation of the bioreductive cytotoxins SR 4895 and SR 4941"; Registry No. 71503-85-0.
CA 129:339530 & Anti-cancer drug design, 1998, vol. 13(6), pp. 575-592, A.B. Kelson et al; "1,2,4-benzotriazine 1,4-dioxides. An important class of hypoxic cytotoxins with antitumor activity"; Registry Nos. 71503-85-0, 166182-18-9, 215535-68-5, 215535-71-0.
CA 138:130592 & Journal of Medicinal Chemistry, 2003, vol. 46(1), pp. 169-182, M.P. Hay et al; "Structure-activity relationships of 1,2,4-benzotriazine 1,4-dioxides as hypoxia-selective analogues of tirapazamine"; Registry No. 50476-99-8.
International Journal of Radiation Oncology Biol. Phys. 1992, vol. 22, No. 4, pp. 701-705, A.I. Minchinton et al; "Second-generation 1,2,4-benzotriazine 1,4-di-N-oxide bioreductive anti-tumor agents: Pharmacology and activity in vitro and in vivo".
Supplementary European Search Report; International Application No. EP 05 72 2109, dated Oct. 5, 2009 (2 pgs).
Hay, M.P., et al; Hypoxia-Selective 3-Alkyl 1,2,4-Benzotriazine 1,4-Dioxides: The Influence of Hydrogen Bond Donors on Extravascular Transport and Antitumor Activity; J. Med. Chem..; vol. 50, pp. 6654-6664 (2007).
Shinde, S.S., et al; Oxidation of 2-Deoxyribose by Benzotriazinyl Radicals of Antitumor 3-Amino-1,2,4-benzotriazine 1,4-Dioxides; J. Am. Chem. Soc.; vol. 126; pp. 7865-7874 (2004) XP-002547140.

* cited by examiner

*Primary Examiner*—Venkataraman Balasubramanian
(74) *Attorney, Agent, or Firm*—Nixon & Vanderhye

(57) ABSTRACT

The compound 3-ethyl-6-[3-(4-morpholinyl)propoxy]-1,2,4-benzotriazine 1,4-dioxide and pharmacologically acceptable salts thereof. A method of treating cancer in a subject is also described in which 3-ethyl-6-[3-(4-morpholinyl)propoxy]-1, 2,4-benzotriazine 1,4-dioxide or a pharmacologically acceptable salt thereof is administered to tumor cells in a hypoxic environment. Also described is a method of radiosensitising in a subject tumor cells of solid tumors in hypoxic conditions by administering to the subject a pharmaceutical composition containing 3-ethyl-6-[3-(4-morpholinyl)propoxy]-1,2,4-benzotriazine 1,4-dioxide or a pharmacologically acceptable salt thereof in an amount sufficient to produce radiosensitivity in the tumor cells, and subjecting the tumor cells to radiation. A pharmaceutical composition is additionally provided containing a therapeutically effective amount of 3-ethyl-6-[3-(4-morpholinyl)propoxy]-1,2,4-benzotriazine 1,4-dioxide or a pharmacologically acceptable salt thereof and a pharmaceutically acceptable excipient, adjuvant, carrier, buffer or stabiliser.

6 Claims, 5 Drawing Sheets

A

B

1,2,4-BENZOTRIAZINE-1,4-DIOXIDES

REFERENCE TO GOVERNMENT CONTRACT

The invention described herein was made in the course of work under grant or contract from the United States Department of Health and Human Services. The United States Government has certain rights to this invention.

This application is the U.S. National Phase of International Application PCT/NZ2005/000034, filed 1 Mar. 2005, which designated the U.S. PCT/NZ2005/000034 claims priority to New Zealand Application No. 531499 filed 1 Mar. 2004. The entire content of these applications are incorporated herein by reference.

TECHNICAL FIELD

The present invention provides a simplified set of characteristics that can be used to select 1,2,4 benzotriazine 1,4 dioxide compounds (TPZ analogues) with therapeutic activity against hypoxic cells in human tumour xenografts, and to further provide a novel class of 1,2,4-benzotriazine-1,4-dioxides (TPZ analogues) with predicted in vivo activity against tumours, to their preparation, and to their use as hypoxia-selective cytotoxic drugs and radiosensitizers for cancer therapy, both alone or in combination with radiation and/or other anticancer drugs.

BACKGROUND TO THE INVENTION

It has been established that many human tumors contain a significant hypoxic fraction of cells [Kennedy et al., *Int. J. Radiat. Oncol. Biol. Phys.*, 1997, 37, 897; Movsas et al., *Urology*, 1999, 53, 11]. The presence of hypoxic cells arises because the extravascular transport (EVT) of oxygen is compromised due to an inefficient microvascular system within the tumor, which leads to large intercapillary distances and variable blood flow. Reduction of oxygen tension in tumors leads to radio-resistance. This reduction of oxygen tension causes up to a three-fold increase in radiation dose being required to kill anoxic tumour cells. A link has been identified between the presence of tumour hypoxia and failure of local control by radiation therapy [Brizel et al., *Radiother. & Oncol.*, 1999, 53, 113].

This phenomenon of tumour hypoxia has been exploited in the development of 'bioreductive drugs' [Brown et al., *Semin. Radiat. Oncol.* 1966, 6, 22; Denny et al., *Br. J. Cancer*, 1996, 74 (*Suppl. XXVII*) 32; Stratford & Workman, *Anti-Cancer Drug Des.*, 1998, 13, 519]. These agents are prodrugs that are selectively activated by enzymatic reduction in hypoxic cells, resulting in formation of a cytotoxin.

The 3-amino-1,2,4-benzotriazine 1,4-dioxides have been developed as bioreductive drugs for cancer therapy [Brown, *Br. J. Cancer*, 1993, 67, 1163-1170; Minchinton et al., *Int. J. Radiat. Oncol. Biol. Phys.* 1992, 22, 701-705 Kelson et al., *Anti-Cancer Drug Des.*, 1998, 13, 575; Lee et al., WO 91/04028, April 1991]. The lead compound of this class, tirapazamine (TPZ; SR 4233), is undergoing clinical trials in combination with radiotherapy and various chemotherapeutics, notably cisplatin [Denny & Wilson, *Exp. Opin. Invest. Drugs*, 2000, 9, 2889]. TPZ is activated by one electron reductases [Patterson et al., *Anti-Cancer Drug Des.* 1998 13, 541; Denny & Wilson, *Exp. Opin. Invest. Drugs*, 2000, 9, 2889] to form a radical that may be oxidized back to TPZ by molecular oxygen under aerobic conditions. Under hypoxic conditions the radical spontaneously generates an oxidizing radical(s) R• (considered to be the hydroxyl radical [Daniels and Gates, *J. Am. Chem. Soc.*, 1996, 118, 3380-3385], and/or a benzotriazinyl radical [Anderson et al., *J. Am. Chem. Chem.* 2003, 125, 748-756]) which interact with DNA (and/or topoisomerase II)[Peters and Brown, *Cancer Res.*, 2002, 62, 5248-5253] to cause double-strand breaks and these correlate with cytotoxicity [Dorie et al., *Neoplasia*, 1999, 1, 461]. These features are illustrated in Scheme 1.

Scheme 1: Mechanism of action of TPZ

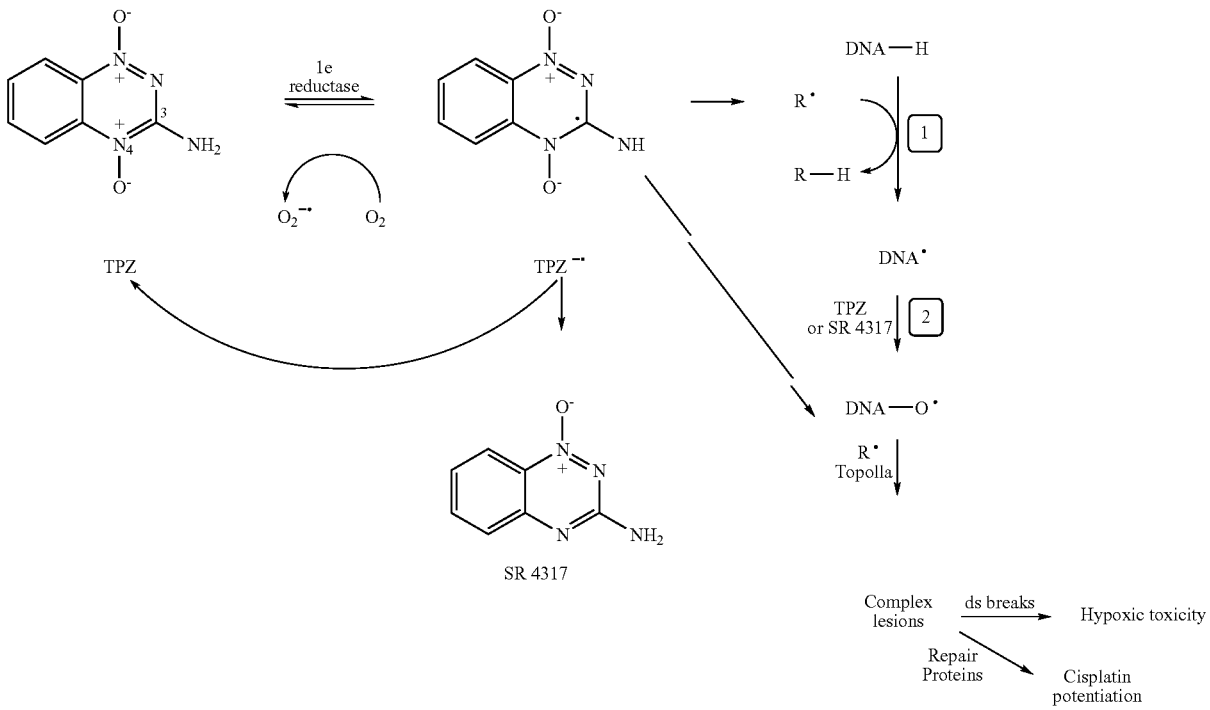

There have been only limited structure-activity studies on analogues of TPZ. Kelson et al. [*Anti-Cancer Drug Design*, 1998, 13, 575], Zeman et al. [*Int. J. Radiat. Oncol. Biol. Phys.*, 1989, 16, 977-981] and Minchinton et al. [*Int. J. Radiat Oncol. Biol. Phys.*, 1992, 22, 701-705] disclosed compounds of type I,

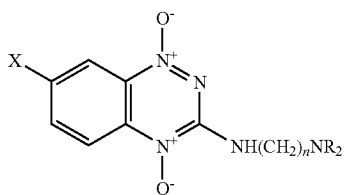

where X was H or an electron-withdrawing group, n was 2 or 3, and R was Me or Et. This paper showed that compounds with dialkylaminoalkyl side chains showed variable hypoxic selectivity in vitro. Compounds where X=H and having dialkylamino side chains had a similar hypoxic cytotoxicty ratio to TPZ and comparable or inferior activity to TPZ in vivo.

Hay and Denny [*Tet. Lett.*, 2002, 43, 9569], Minchinton et al. [*Int. J. Radiat. Oncol. Biol. Phys.*, 1992, 22, 701-705] and Kelson et al. [*Anti-Cancer Drug Design*, 1998, 13, 575] described compounds of type II,

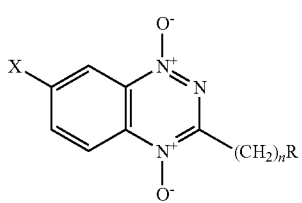

where X is H or hydroxyalkyl and R is OH or OMe. Kelson et al. [*Anti-Cancer Drug Design*, 1998, 13, 575] and Minchinton et al., [*Int. J. Radiat. Oncol. Biol Phys.*, 1992, 22, 701-705] suggested that 3-alkyl compounds (X=H, n=1,2 or 3, R=H and X=H, n=2, R=OMe) were comparable to TPZ in vivo.

Finally, Hay et al. [Hay et al., *J. Med. Chem.* 2003, 46, 169] showed, for compounds of type III,

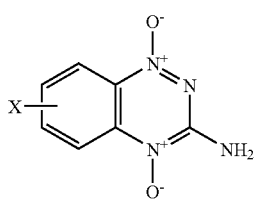

that there is an optimum range of one-electron reduction potential [E(1)] (between ca. −450 to −510 mV) for in vitro hypoxic selectivity. However, there was no clear relationship between the electron-withdrawing capability of the 7-substituent on the benzo ring and the reported biological activity.

Throughout this specification several abbreviations are used that require explanation and the following glossary is provided.

$IC_{50}$: The concentration of drug (in micromolar, μM) to reduce cell numbers to 50% of those of control cell cultures grown under the same conditions but not exposed to drug.

HCR: Hypoxic cytotoxicity ratio (the ratio of drug concentrations under aerobic and hypoxic conditions to produce equal cell survival (50%) determined by proliferation assay)

Kmet: First order rate constant for metabolism of a drug estimated at the $C_{10}$ (see below)

$C_{10}$: the concentration required to produce one log of cell kill after exposure of cells to drug for one hour in clonogenic assays described in the methods (below).

PK: Pharmacokinetics. (Description of the variation in drug concentration with time (i.e. exposure) in a specified compartment or position within a tissue)

PD: Pharmacodynamics. (Description of the biological response to a drug)

PK/PD Model: Mathematical description of the relationship between drug exposure (PK) and biological response (PD).

Drawbacks of TPZ

Despite its advancement in clinical trials, several limitations of TPZ have been identified, including its relatively low solubility and poor therapeutic ratio. It is clear that the therapeutic ratio of TPZ in both preclinical (murine and human tumours) and clinical studies is low, with substantial toxicity at efficacious doses [Rischin et al., Proc. Am. Soc. Clin. Oncol. 2003, 22, 495-496] and that there is a need for more tumour selective analogues. Preclinical studies have identified extravascular transport (EVT) as a factor that limits activity of TPZ against hypoxic cells in tumours [Durand & Olive Radiat. Oncol. Investig. 1997, 5, 213; Durand & Olive, *Int. J. Radiat. Oncol. Biol. Phys.* 1992, 22, 689; Hicks et al, *Int. J. Radiat. Oncol. Biol. Phys.* 1998, 42, 641; Hicks et al, *Cancer Res.* 2003, 63, 5970; Kyle & Minchinton, *Cancer Chemother. Pharmacol.* 1999, 43, 213].

The EVT problem is thought to be particularly severe for bioreductive drugs, such as TPZ, for two reasons:
1. The target hypoxic cells are generally those most distant from the blood vessels
2. The metabolism of the bioreductive drug in the hypoxic tumour tissue will cause a continuously falling gradient of drug concentration through both the oxic and hypoxic tumour tissue which may not be overcome even with long infusion times.

However the same bioreductive metabolism which limits drug transport is also responsible for the cytotoxic effect of the drug [Baker et al. *Cancer Res.*, 1988, 48, 5947-5952; Siim et al, *Br. J. Cancer* 1996, 73, 952]. These competing effects of drug metabolism on EVT and cytotoxicity have been investigated using the multicellular layer model [Hicks et al, *Int. J. Radiat. Oncol. Biol. Phys.* 1998, 42, 641], as illustrated in FIG. 1. Parameters determined by this model, together with single cell experiments to determine cytotoxicity and rates of metabolism [Hicks et al, *Cancer Res.* 2003, 63, 5970] and the oxygen dependence of cytotoxicity [Hicks et al., *Radiat. Res.* 2004, 161, 656] are used in a pharmacokinetic/pharmacodynamic (PK/PD) model of cell killing in tumour tissue (as illustrated in FIG. 2). The model and results obtained have demonstrated the need to optimise (rather than maximise) the rate of bioreductive metabolism. FIG. 2 illustrates that high rates of metabolism will limit drug penetration and thus reduce cell kill in the hypoxic region, as well as decrease the differential in killing of hypoxic cells compared to well oxygenated cells. This is consistent with experimental results where high rates of metabolism limited activity in anoxic V79 multicellular spheroids [Durand & Olive *Int. J. Radiat. Oncol. Biol. Phys.* 1992, 22, 689] and anoxic HT29 MCL [Hicks et al., *Cancer Res.* 2003, 63, 5970], and resulted in a reduced hypoxic cytotoxic differential in SiHa human cervical tumours grown in SCID mice [Durand & Olive, *Radiat. Oncol. Investig.* 1997, 5, 213].

The above PK/PD model for TPZ, developed by Hicks et al., can be described as a distributed parameter model because it considers explicitly the spatial variation in parameter values (in other words it describes PK, and PD, as a function of position in tumour tissue). The main aspects of this distributed parameter PK/PD model have been disclosed in several publications (Hicks et al., *Int. J. Radiat. Oncol. Biol. Phys.* 1998, 42, 641; Hicks et al., *Cancer Res.* 2003, 63, 5970; Hicks et al., *Proc Am. Assoc. Cancer Res*, 2003, Abstract #4561; Wilson et al., *Proc Am. Assoc. Cancer Res*, 2003, Abstract #4570).

The key PK/PD relationship, as determined by investigating TPZ metabolism to its reduction product SR 4317 and cell killing as a function of TPZ concentration and time in anoxic stirred suspensions of HT29 colon carcinoma cells (Hicks et al., *Cancer Res.*, 2003), is described by:

Eqn 1:
$$-\frac{d\log SF}{dt} = \gamma C \frac{dM}{dt}$$

This relationship shows that the rate at which cells are killed (on a log scale; SF=surviving fraction) is proportional to the rate of bioreductive drug metabolism (M, the amount of drug metabolised per unit intracellular volume) and to the drug concentration, C. The constant of proportionality, $\gamma$, is a cell-line dependent parameter determined by fitting the model to clonogenic survival curves where drug concentrations are measured simultaneously. Under conditions of constant TPZ concentration, this approximates a concentration$^2 \times$ time dependence of log cell kill on TPZ exposure.

In order to describe PK/PD as a function of position in tumours, the above PK/PD model is extended to a spatially resolved (distributed parameter) model by incorporating the EVT properties (diffusion coefficient and rate of metabolism) of TPZ. In addition, because oxygen concentration in tumours varies as a function of distance from blood vessels, it is necessary to describe the relationship between $O_2$ concentration and rate of TPZ metabolism.

Simulation of TPZ diffusion into a tumour—in one dimension is illustrated in (FIG. 3A. An $O_2$ concentration gradient in the one dimension planar tissue can be calculated numerically by solving the reaction-diffusion equation:

Eqn 2:
$$\frac{\partial C_{O_2}}{\partial t} = D_{O2}\frac{\partial^2 C_{O_2}}{\partial x^2} - \frac{\partial C_{O_2}}{\partial t}$$

where $C_{O_2}$ is the oxygen concentration in $\mu$M at position x and time t, using the diffusion coefficient and rate of metabolism in R3230Ac tumors (Dewhirst et al., *Cancer Res.*, 1994, 54, 3333; Secomb et al., *Adv. Exp. Med. Biol.* 1998, 454, 629) assuming an arteriolar input oxygen concentration of $[O_2]$= 50 $\mu$M (38 mm Hg).

TPZ concentrations in the one dimensional tissue are calculated numerically from the reaction diffusion equation:

Eqn 3:
$$\frac{\partial C}{\partial t} = D_{MCL}\frac{\partial^2 C}{\partial x^2} - \phi f([O_2])\frac{\partial M}{\partial t}$$

where C is the concentration of drug at position x and time t, $D_{MCL}$ is the diffusion coefficient of drug in the multicellular layers, and $\phi$ is the cell volume fraction of the multicellular layer. Oxygen inhibits TPZ metabolism and this effect can be calculated according to the equation:

Eqn 4:
$$f([O_2]) = \left(\frac{K_{O_2}}{K_{O_2} + [O_2]}\right)$$

where $K_{O_2}$ is the $O_2$ concentration required for half maximal inhibition of TPZ metabolism.

The above relationships (Eqn 1-4) define a PK/PD model for TPZ. The output of the model depends on the plasma PK of free drug (drug not bound to plasma proteins), which provides the input to the extravascular compartment, and on the geometry of the transport problem. Using this model the surviving fraction at each point in the tissue is calculated and the average log cell kill in the target hypoxic region evaluated. This is illustrated in FIG. 2 for TPZ at its maximum tolerated in mice, together with simulations for a faster diffusing drug and an analogue with higher rates of metabolic activation.

This PK/PD model can be further extended to take into account the effects of diffusion in a three dimensional-3D microvascular environment, such as irregular vascular geometry, blood flow heterogeneity, and loss of oxygen and drug during transit through a capillary network. Such a 3D network is illustrated in FIG. 3B and further described in (Hicks et al., *Proc Am. Assoc. Cancer Res*, 2003, Abstract #4561; Wilson et al., *Proc Am. Assoc. Cancer Res*, 2003, Abstract #4570). In this model similar equations as Eqns 1-4 are solved numerically using a Green's function method similar to that used for oxygen alone (Secomb et al., *Adv. Exp. Med. Biol.* 1998, 454, 629).

In order to test the validity of this PK/PD model as a tool for predicting the antitumour activity of TPZ analogues, the inventors determined the key PK/PD parameters for 13 TPZ analogues, and TPZ itself, for the HT29 human colon carcinoma cell line. These parameters were then used to calculate the expected killing in hypoxic regions of HT29 tumours following a single intraperitoneal dose of the compounds at their maximum tolerated dose. The results of this calculation were then compared with measured killing of hypoxic cells in HT29 tumours, determined by administering the compounds immediately (within 5 min) after gamma irradiation (cobalt 60, 20 Gy) to sterilise oxygenated cells in the tumours. Tumours were removed 18 hours later and the number of surviving cells determined by clonogenic assay. The results for one compound 3 are shown in FIG. 5. The measured PK/PD parameters, model prediction (using the above 3D microvascular network), and experimentally determined hypoxic cell kill is shown in Table 1, and the relationship between predicted and measured cell kill in FIG. 4. The prediction is statistically highly significant (p=0.001, Fisher exact test). Comparing the magnitude of predicted and observed response (FIG. 4) also shows a highly significant linear correlation ($R^2=0.94$, $p<0.001$ for a non-zero slope). If the extravascular transport component was excluded from the model, the $R^2$ for this regression was only 0.28 and the relationship was not statistically significant.

TABLE 1

Parameters of the PK/PD model for 14 benzotriazine di-N-oxides, model prediction of hypoxic cell killing in tumours, and measured hypoxic cell killing.

| Cmpd | $D_{MCL}$ cm$^2$s$^{-1}$ | $k_{met}$ min$^{-1}$ | $\gamma$ µM$^2$ | AUC$_f$ µM.hr | log kill (Pred) | log kill (Meas) | SE | Stat. Signif. |
|---|---|---|---|---|---|---|---|---|
| A | $3.97 \times 10^{-7}$ | 0.60 | $2.21 \times 10^{-5}$ | 148.1 | 1.248 | 1.170 | 0.149 | <0.01 |
| B | $5.43 \times 10^{-7}$ | 0.20 | $1.64 \times 10^{-5}$ | 188.7 | 1.923 | 2.165 | 0.149 | <0.01 |
| C | $8.70 \times 10^{-7}$ | 3.92 | $3.71 \times 10^{-5}$ | 1.9 | 0.005 | —0.007 | 0.184 | ns |
| D | $6.69 \times 10^{-7}$ | 10.03 | $2.25 \times 10^{-6}$ | 0.8 | 0.000 | —0.154 | 0.064 | ns |
| E | $2.13 \times 10^{-7}$ | 1.00 | $1.40 \times 10^{-6}$ | 15.6 | 0.000 | —0.028 | 0.083 | ns |
| F | $5.09 \times 10^{-7}$ | 2.54 | $6.84 \times 10^{-5}$ | 3.5 | 0.011 | 0.196 | 0.062 | ns |
| G | $1.71 \times 10^{-6}$ | 4.89 | $3.90 \times 10^{-5}$ | 7.2 | 0.048 | 0.248 | 0.072 | ns |
| H | $3.99 \times 10^{-7}$ | 1.52 | $1.10 \times 10^{-4}$ | 69.0 | 0.985 | 1.001 | 0.142 | <0.01 |
| I | $2.61 \times 10^{-6}$ | 1.91 | $6.52 \times 10^{-6}$ | 140.6 | 1.116 | 0.886 | 0.132 | <0.01 |
| J | $2.09 \times 10^{-6}$ | 2.01 | $2.90 \times 10^{-4}$ | 79.0 | 0.890 | 0.800 | 0.149 | <0.05 |
| K | $6.17 \times 10^{-7}$ | 18.33 | $9.86 \times 10^{-3}$ | 0.042 | 0.000 | 0.009 | 0.102 | ns |
| L | $3.82 \times 10^{-7}$ | 9.18 | $1.30 \times 10^{-3}$ | 3.6 | 0.078 | -0.051 | 0.039 | ns |
| M | $9.80 \times 10^{-8}$ | 9.13 | $3.04 \times 10^{-3}$ | 0.9 | 0.056 | 0.138 | 0.100 | ns |
| N | $1.05 \times 10^{-7}$ | 4.74 | $2.39 \times 10^{-2}$ | 1.3 | 0.092 | 0.027 | 0.121 | ns |

AUC$_f$ = AUC of free drug
Log kill (Pred) = -log$_{10}$ (hypoxic cell surviving fraction) predicted by the model
Log kill (Meas) = -log$_{10}$ (hypoxic cell surviving fraction) measured in tumours
SE = standard error of log kill (Meas).
Stat. Signif. = statistical significance of log kill (Meas).

A

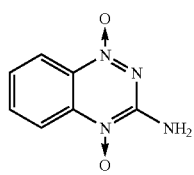

B

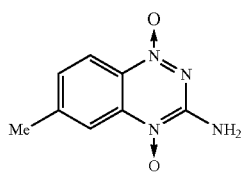

C

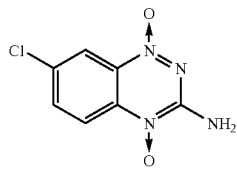

D

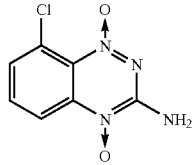

E

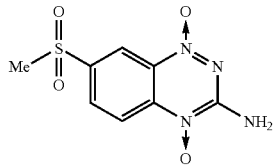

TABLE 1-continued

Parameters of the PK/PD model for 14 benzotriazine di-N-oxides, model
prediction of hypoxic cell killing in tumours, and measured hypoxic cell killing.

| Cmpd | $D_{MCL}$ cm$^2$s$^{-1}$ | $k_{met}$ min$^{-1}$ | $\gamma$ $\mu M^2$ | $AUC_f$ $\mu M.hr$ | log kill (Pred) | log kill (Meas) | SE | Stat. Signif. |
|---|---|---|---|---|---|---|---|---|

F

G

H

I

J

K

L

TABLE 1-continued

Parameters of the PK/PD model for 14 benzotriazine di-N-oxides, model prediction of hypoxic cell killing in tumours, and measured hypoxic cell killing.

| Cmpd | $D_{MCL}$ cm$^2$s$^{-1}$ | $k_{met}$ min$^{-1}$ | $\gamma$ $\mu M^2$ | $AUC_f$ $\mu$M.hr | log kill (Pred) | log kill (Meas) | SE | Stat. Signif. |
|---|---|---|---|---|---|---|---|---|

M

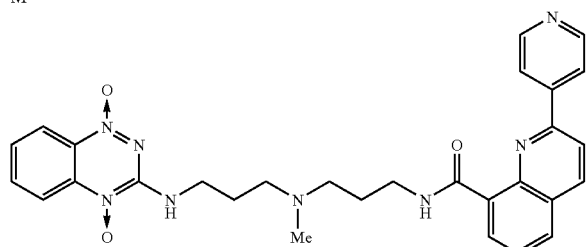

N

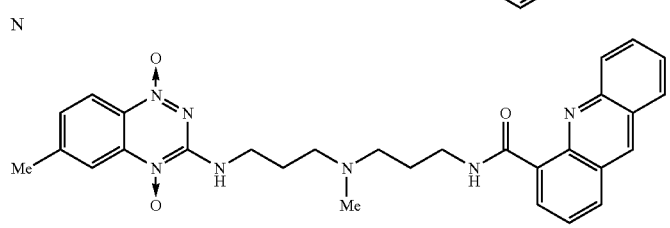

It is established by these studies that extravascular transport is a determinant of in vivo cytotoxicity and selectivity of benzotriazine di-N-oxides. These results confirm that the measurement of parameters such as IC$_{50}$ and HCR in cell culture, alone, do not provide a reliable prediction for activity against hypoxic cells in tumours.

However, despite the elegance of these models and the highly statistically significant results achieved, one of the inherent difficulties with this approach is that it requires complex computational methods, and a detailed knowledge of a microvascular network geometry and blood flow. This information is not generally available.

It is therefore an object of the present invention to overcome some of these complexities by providing a simplified set of characteristics that can be used to select 1,2,4 benzotriazine 1,4 dioxide compounds (TPZ analogues) with therapeutic activity against hypoxic cells in human tumour xenografts, and to provide a method by which these characteristics can be assessed with minimal or no testing of the compounds in animals and to further provide a novel class of TPZ analogues with predicted improved in vivo activity against tumours, relative to TPZ, or to at least provide the public with a useful choice.

DISCLOSURE OF THE INVENTION

In a first aspect the present invention provides a method of selecting one or more 1,2,4-benzotriazine-1,4-dioxides capable of in vivo hypoxia selective cytotoxicity, wherein said 1,2,4-benzotriazine-1,4-dioxide is selected if it is determined to have each of the following characteristics
  (a) a solubility greater than or about 2 mM in culture medium; and
  (b) an HT29 anoxic IC$_{50}$ for a 4 hr exposure to the 1,2,4-benzotriazine-1,4-dioxide of less than or about 40 $\mu$M; and
  (c) a hypoxic cytotoxicity ratio (HCR) greater than about 20 for the HT29 cell line; and
  (d) a penetration half distance (PHD) greater than or about 27 $\mu$m, and (e) the area under the plasma concentration time curve for free 1,2,4-benzotriazine-1,4-dioxide (unbound to plasma proteins), AUC$_f$, is greater than about 2 times the HT29 anoxic IC$_{50}$×t where IC$_{50}$×t is the product of concentration×exposure time for 50% inhibition of cell proliferation and wherein for said 1,2,4-benzotriazine-1,4-dioxide at least one of the characteristics (a) to (e) exceeds the activity of the equivalent characteristic of Tirapazamine.

It is to be appreciated that in most cases the AUC$_f$ would be measured at a tolerable dose of drug in animals for compounds that pass the first three rules of the first aspect defined above or the first four rules of the alternative aspect defined above. (although AUC$_f$ can also be estimated by calculation as noted below). The algorithm increases the chance that selected compounds will have utility as anticancer agents, making it possible to eliminate compounds from the testing pipeline without undertaking expensive and time-consuming therapy studies in animals.

It has been found that many 1,2,4-benzotriazine-1,4-dioxide compounds can be rejected because they fail criterion (a) or (b) or (c) hence avoiding the need to test those compounds in vivo since the PK criterion then becomes irrelevant.

In a further aspect, the invention provides a 1,2,4-benzotriazine-1,4-dioxide (TPZ analogue) selected by either of the methods defined above with the proviso that Tirapazamine and compounds of Formula I and J

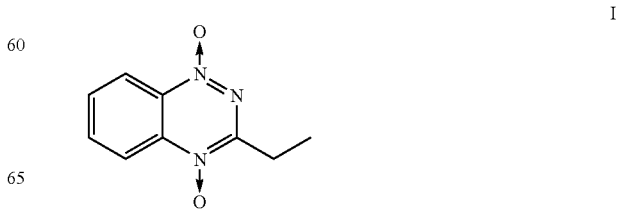

I

-continued

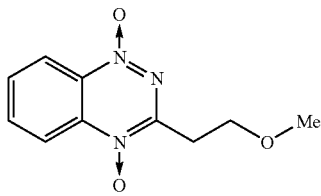

J are excluded.

Preferably, the 1,2,4-benzotriazine-1,4-dioxide compound selected by the method defined above is selected from
$N^1,N^1$-Dimethyl-$N^2$-(6-methyl-1,4-dioxido-1,2,4-benzotriazin-3-yl)-1,2-ethanediamine;
6-Methyl-N-[3-(4-morpholinyl)propyl]-1,2,4-benzotriazin-3-amine 1,4-dioxide;
$N^1$-(6-Methoxy-1,4-dioxido-1,2,4-benzotriazin-3-yl)-$N^2$,$N^2$-dimethyl-1,2-ethanediamine;
$N^1$-[6-(2-Methoxyethoxy)-1,4-dioxido-1,2,4-benzotriazin-3-yl]-$N^2$,$N^2$-dimethyl-1,2-ethanediamine;
$N^1,N^1$-Dimethyl-$N^2$-(6-ethoxy-1,4-dioxido-1,2,4-benzotriazin-3-yl)-1,2-ethanediamine;
6-Ethyl-N-[3-(4-morpholinyl)propyl]-1,2,4-benzotriazin-3-amine 1,4-dioxide;
2-[(3-Ethyl-1,4-dioxido-1,2,4-benzotriazin-6-yl)oxy]-N,N-dimethylethaneamine;
3-Ethyl-6-[3-(4-morpholinyl)propoxy]-1,2,4-benzotriazine 1,4-dioxide;
6-Methyl-1,2,4-benzotriazin-3-amine 1,4-dioxide; and their pharmacologically acceptable salts thereof.

In a preferred embodiment there is also provided method of therapy for treating cancer including the step of administering a 1,2,4-benzotriazine-1,4-dioxide compound as defined above in a therapeutically effective amount to tumour cells in a subject. Preferably, the tumour cells are in a hypoxic environment. More preferably the method further includes the step of administering radiotherapy to the tumour cells before, during or after the administration of the 1,2,4-benzotriazine-1,4-dioxide compound as defined above to the tumour cells.

The method can also include the step of administering one or more chemotherapeutic agents, such as Cisplatin or other platinum-based derivatives, Temozolomide or other DNA methylating agents, cyclophosphamide or other DNA alkylating agents, Doxorubicin, mitoxantrone, camptothecin or other topoisomerase inhibitors, Methotrexate, gemcitabine or other antimetabolites and/or Docetaxel or other taxanes to the tumour cells before, during or after the administration of the 1,2,4-benzotriazine-1,4-dioxide compound as defined above to the tumour cells.

In another embodiment there is provided a method of radiosensitising in a subject tumour cells of solid tumours in hypoxic conditions in vivo, comprising the steps of:
(a) administering to the subject a pharmaceutical composition in an amount sufficient to produce radiosensitivity in the tumour cells, the composition comprising a 1,2,4-benzotriazine-1,4 dioxide obtained by either of the methods defined above, and
(b) subjecting the tumour cells to radiation.

In another embodiment, there is provided the use in the manufacture of a medicament of a therapeutically effective amount of a 1,2,4-benzotriazine-1,4-dioxide compound as defined above for the treatment of tumour cells in a subject. Preferably, the tumour cells are in a hypoxic environment.

There is also provided in a further embodiment a pharmaceutical composition including a therapeutically effective amount of a 1,2,4-benzotriazine-1,4-dioxide as defined above and a pharmaceutically acceptable excipient, adjuvant, carrier, buffer or stabiliser.

In a further aspect of the present invention there is provided a 1,2,4-benzotriazine-1,4-dioxide of Formula I or a pharmacologically acceptable salt thereof, selected by the method defined above and having the characteristics (a) to (e) defined above,

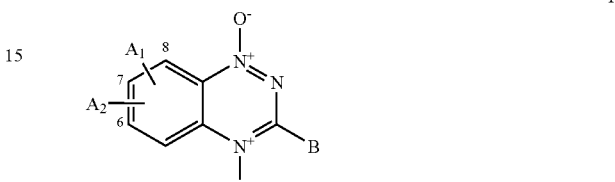

I wherein $A_1$ or $A_2$ represent independently an H or R substituent at positions 6, 7 or 8 and/or an OR substituent at positions 6 or 8
wherein each R independently represents a $C_{1-4}$ alkyl or cyclic $C_3$-$C_8$ alkyl optionally substituted with substituents selected from OH, OMe, or $NR^1R^1$ and wherein each $R^1$ is independently selected from H or a $C_{1-3}$ alkyl or the $R^1R^1$ substituents together form a morpholine ring;
B represents $NHR^2$ or $R^3$;
wherein $R^2$ is a $C_{1-3}$ alkyl optionally substituted with substituents selected from OH, OMe, or $NR^4R^4$
wherein $R^3$ is selected from a $C_{1-3}$ alkyl optionally substituted with OH, OMe,
wherein each $R^4$ is independently selected from H, a $C_{1-3}$ alkyl optionally substituted with OMe, or $R^4R^4$ together form a morpholine ring; and with the proviso that $A_1$ and $A_2$ do not both represent H when B represents $CH_2CH_3$ or $CH_2CH_2OCH_3$; and
with the further proviso that when $A_1$ represents H and $A_2$ represents 7-Me then B cannot represent $NH(CH_2)_2NMe_2$ In another aspect, the present invention provides a compound of Formula I or a pharmacologically acceptable salt thereof,

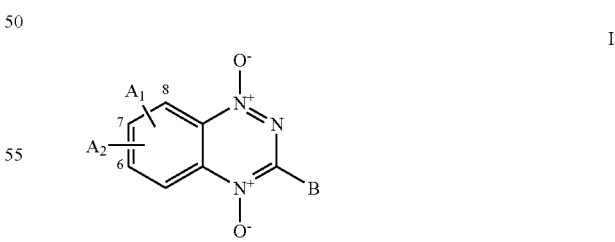

I wherein $A_1$ or $A_2$ represent independently an H or R substituent at positions 6, 7 or 8 and/or an OR substituent at positions 6 or 8
wherein each R independently represents a $C_{1-4}$ alkyl or cyclic $C_3$-$C_8$ alkyl optionally substituted with substituents selected from OMe, or $NR^1R^1$ and wherein each $R^1$ is independently selected from H or a $C_{1-3}$ alkyl or the $R^1R^1$ substituents together form a morpholine ring;

B represents $NHR^2$ or $R^3$;

wherein $R^2$ is a $C_{1-3}$ alkyl optionally substituted with substituents selected from OH, OMe, or $NR^4R^4$ wherein $R^3$ is selected from a $C_{1-3}$ alkyl optionally substituted with OH, OMe, wherein each $R^4$ is independently selected from H, a $C_{1-3}$ alkyl or $R^4R^4$ together form a morpholine ring; and with the proviso that $A_1$ and $A_2$ do not both represent H when B represents $CH_2CH_3$ or $CH_2CH_2OCH_3$; and with the further proviso that when $A_1$ represents H and $A_2$ represents 7-Me then B cannot represent $NH(CH_2)_2NMe_2$.

Preferably, in a compound of Formula I defined above $A_1$ represents Me, Et, OMe, OEt, or $OCH_2CH_2OMe$; $A_2$ represents H and B represents Me, Et, $CH_2CH_2OH$, $CH_2CH_2OMe$, $NHCH_2CH_2NMe_2$, $NHCH_2CH_2Nmorpholine$, or $NHCH_2CH_2CH_2Nmorpholine$.

In a further embodiment preferably a compound of Formula I defined above $A_1$ represents $CH_2CH_2NMe_2$, $CH_2CH_2NEt_2$, $CH_2CH_2Nmorpholine$, $CH_2CH_2CH_2Nmorpholine$, $OCH_2CH_2NMe_2$, $OCH_2CH_2NEt_2$, $OCH_2CH_2Nmorpholine$, or $OCH_2CH_2CH_2Nmorpholine$ and B represents Me, Et, $CH_2CH_2OH$ or $CH_2CH_2OMe$.

In a further embodiment the invention provides for the use in a method of therapy for treating cancer including the step of administering a compound of Formula I as defined above in a therapeutically effective amount to tumour cells in a subject.

Preferably, the tumour cells are in a hypoxic environment.

It is preferred that the method of therapy further includes the step of administering radiotherapy to the tumour cells before, during or after the administration of the compound of Formula I as defined above to the tumour cells.

It is preferred that the method of therapy further includes the step of administering one or more chemotherapeutic agents to the tumour cells before, during or after the administration of the compound of Formula I as defined above to the tumour cells.

In another embodiment there is provided a method of radiosensitising in a subject tumour cells of solid tumours in hypoxic conditions in vivo, comprising the steps of:
(a) administering to the subject a pharmaceutical composition in an amount sufficient to produce radiosensitivity in the tumour cells, the composition comprising a 1,2,4-benzotriazine-1,4 dioxide of Formula I as defined above, and
(b) subjecting the tumour cells to radiation.

In a further aspect the invention provides for the use in the manufacture of a medicament of a therapeutically effective amount compound of a Formula I as defined above for the treatment of tumour cells in a subject.

Preferably the tumour cells are in a hypoxic environment.

While these compounds will typically be used in cancer therapy of human subjects, they can be used to target tumour cells in other warm blooded animal subjects such as other primates, farm animals such as cattle, and sports animals and pets such as horses, dogs, and cats.

A "therapeutically effective amount", is to be understood as an amount of a compound of Formula I as defined above or a compound of Formula I' as defined above or a mixture thereof that is sufficient to show benefit to a patient. The actual amount, rate and time-course of administration, will depend on the nature and severity of the disease being treated. Prescription of treatment is within the responsibility of general practitioners and other medical doctors.

A hypoxic environment is to be understood as either an in vitro environment with an oxygen concentration less than 10 μM, or an in vivo environment having a lower oxygen tension than normal tissues.

It is to be understood that the compound of Formula I can be administered alone or in combination with other chemotherapeutic agents or treatments, especially radiotherapy, either simultaneously or sequentially dependent upon the condition to be treated.

Preferred chemotherapeutic agents can be selected from:
Cisplatin or other platinum-based derivatives,
Temozolomide or other DNA methylating agents,
Cyclophosphamide or other DNA alkylating agents,
Doxorubicin, mitoxantrone, camptothecin or other topoisomerase inhibitors,
Methotrexate, gemcitabine or other antimetabolites,
Docetaxel or other taxanes.

In another aspect of the present invention there is provided a pharmaceutical composition including a therapeutically effective amount of a compound of formula I or a mixture thereof, a pharmaceutically acceptable excipient, adjuvant, carrier, buffer or stabiliser.

The pharmaceutically acceptable excipient, adjuvant, carrier, buffer or stabiliser should be non-toxic and should not interfere with the efficacy of the active ingredient.

The precise nature of the carrier or other material will depend on the route of administration, which can be oral, or by injection, such as cutaneous, subcutaneous, or intravenous injection.

Pharmaceutical compositions for oral administration can be in tablet, capsule, powder or liquid form. A tablet may comprise a solid carrier or an adjuvent. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such as gelatin.

For intravenous, cutaneous or subcutaneous injection, the active ingredient will be in the form of a parenterally acceptable aqueous solution which is pyrogen-free and has a suitable pH, isotonicity and stability. Those of relevant skill in the art are well able to prepare suitable solutions using, for example, isotonic vehicles such as Sodium Chloride injection, Ringer's injection, Lactated Ringer's injection. Preservatives, stabilisers, buffers antioxidants and/or other additives may be included as required.

It is to be recognised that certain compounds of the present invention may exist in one or more different enantiomeric or diastereomeric forms. It is to be understood that the enantiomeric or diasteriomeric forms are included in the above aspects of the invention.

The term pharmacologically acceptable salt used throughout the specification is to be taken as meaning any acid or base derived salts formed from hydrochloric, sulfuric, phosphoric, acetic, citric, oxalic, malonic, salicyclic, malic, fumaric, succinic, ascorbic, maleic, methanesulfonic, isoethonic acids and the like and potassium carbonate sodium or potassium hydroxide ammonia, triethylamine, triethanolamine and the like.

BRIEF DESCRIPTION OF THE DRAWINGS

Further aspects of the present invention will become apparent with reference to the following detailed description, the Synthetic Schemes, the Examples; and the Figures, which are given by way of example only, where.

1. A 2-fold increase in the rate of metabolism (and hence 2-fold increase in vitro cytotoxic potency) results in no significant increase in killing in the hypoxic region (O2<4 µM) but gives a 2-fold increase in killing of oxygenated cells near blood vessels. This change is therefore predicted to be therapeutically unfavourable, and demonstrates the importance of optimising (rather than maximising) rates of metabolic reduction of TPZ analogues.
2. A 6-fold increase in the diffusion coefficient, with no increase in the rate of metabolism and hence no increase in in vitro cytotoxic potency, results in a 2-fold increase in cell killing in the hypoxic zone without any undesirable increase in cell killing in the oxic zone. This 2-fold increase in hypoxic selectivity in vivo is predicted to be therapeutically favourable.
3. A 6-fold increase in the diffusion coefficient together with a 2-fold increase in the rate of metabolism (and hence a 2-fold increase in in vitro potency) results in a 3-fold increase in cell killing in the hypoxic zone and a 2-fold increase in in vivo hypoxic selectivity.

Figure 1:
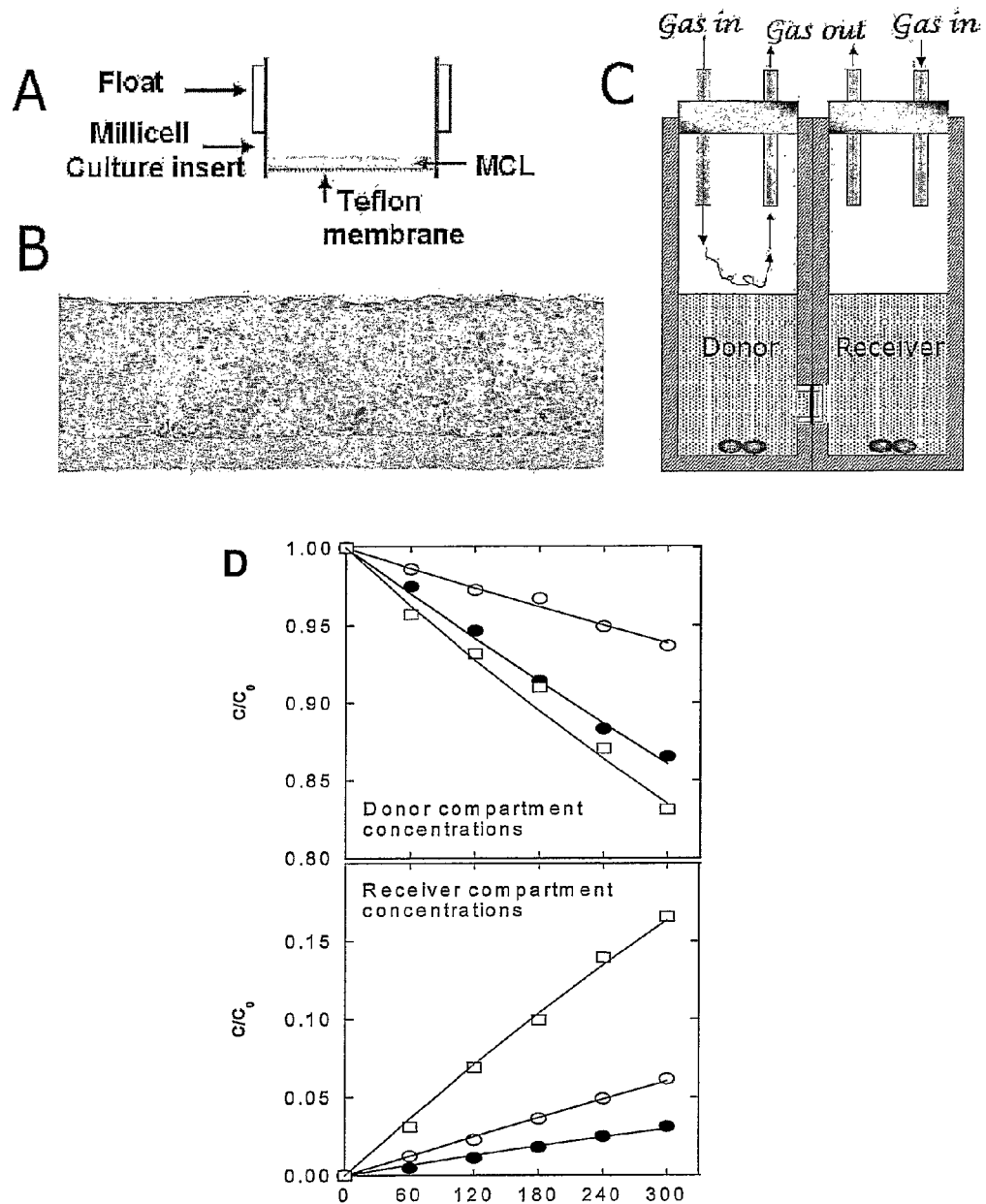
FIG. 1 shows schematically a method for quantifying extravascular transport (EVT) properties of compounds of Formula I using multicellular layers (MCL). A: Diagram of a Millicell® CM culture insert used for growing MCLs on a porous, collagen-coated Teflon membrane. B: H&E-stained transverse section of an HT-29 MCL three days after initiating growth with $10^6$ cells. The Teflon membrane is ca 30 µm thick. C: Diffusion apparatus for measurement of transport through MCLs. D: Diffusion of TPZ (100 µM) through well oxygenated (open circles) and a 2-fold reduction in this diffusion in poorly oxygenated (filled circles) HT29 MCLs of equivalent thickness (141±5 µm). Concentrations are normalized to the initial concentration in the donor compartment ($C_o$). The Lines are fits to a reaction-diffusion model. Also shown is the diffusion of compound #20 through a well oxygenated MCL of a similar thickness illustrating the effect of raising the diffusion coefficient from $4 \times 10^{-7}$ $cm^2 s^{-1}$ to $1.4 \times 10^{-6}$ $cm^2 s^{-1}$.
Figure 2:
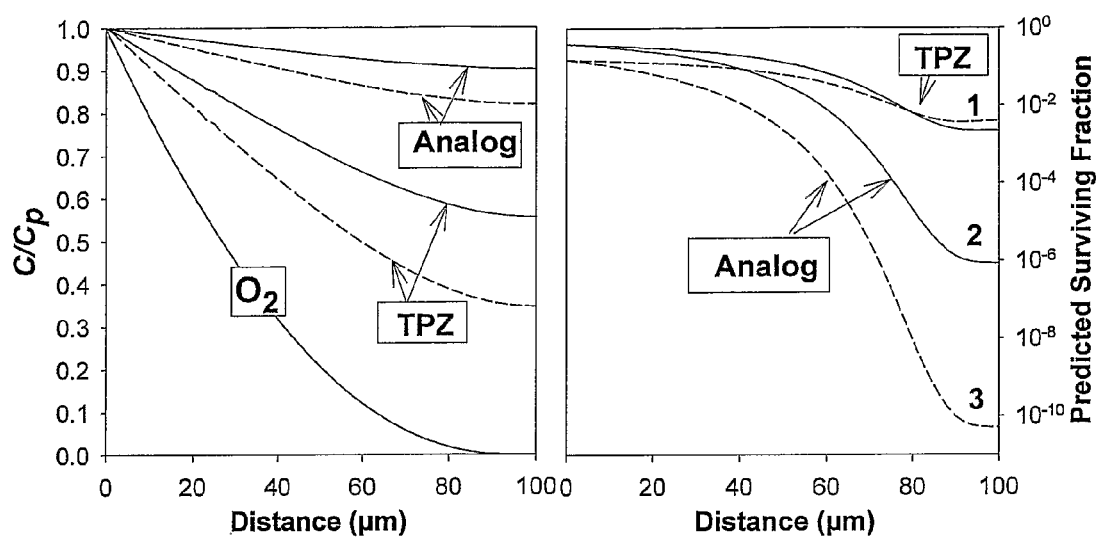
FIG. 2. Illustrates the sensitivity of hypoxic cell killing in tumours to changes in diffusion coefficient of TPZ analogues, simulated using a spatially resolved 1D PK/PD model. The solid lines are based on the measured rate of metabolism of TPZ by HT29 cells, and the dashed line on a two-fold higher rate of metabolism. The Left Panel of FIG. 2 shows steady-state concentration gradients as fractions of the plasma concentration, ($C_p$=50 µM) for $O_2$, TPZ and a TPZ analogue with 6-fold higher diffusion coefficient assuming the same rate of metabolism as for TPZ. The Right Panel of FIG. 2, shows predicted cell killing for the same two compounds. The cytotoxicity parameter (γ) is assumed to have the same value as that found experimentally for TPZ. The numbers on the graph refer to the following situations.
Figure 3:
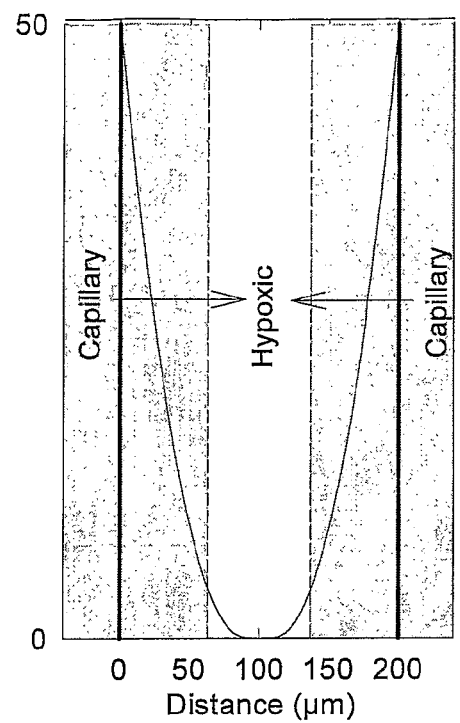
Figure 3:
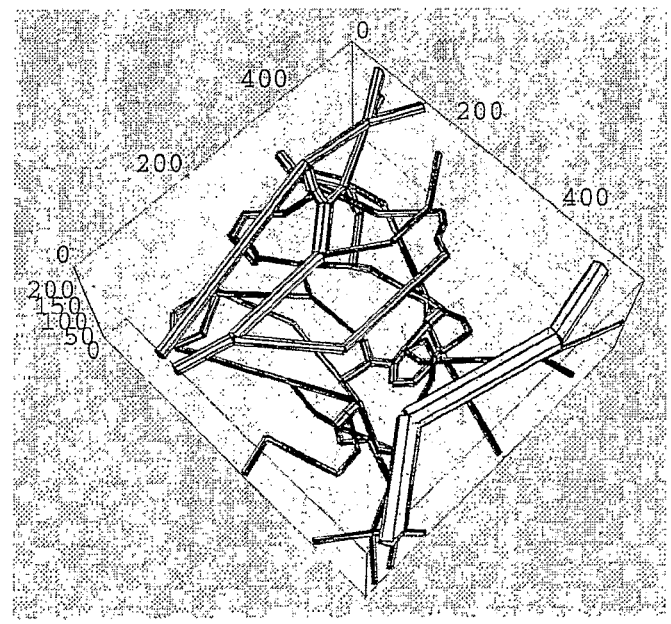

FIG. 3 illustrates the geometry used in the PK/PD model of extravascular transport in tumours. A: illustrates the 1D diffusion into a planar tissue region between two capillaries with a line showing the falling oxygen concentration gradient from the capillary to the center of the region. B: illustrates the 3D diffusion in a mapped microvascular network in a 230×500×500 µm region in a R3230Ac tumour.

Figure 4:
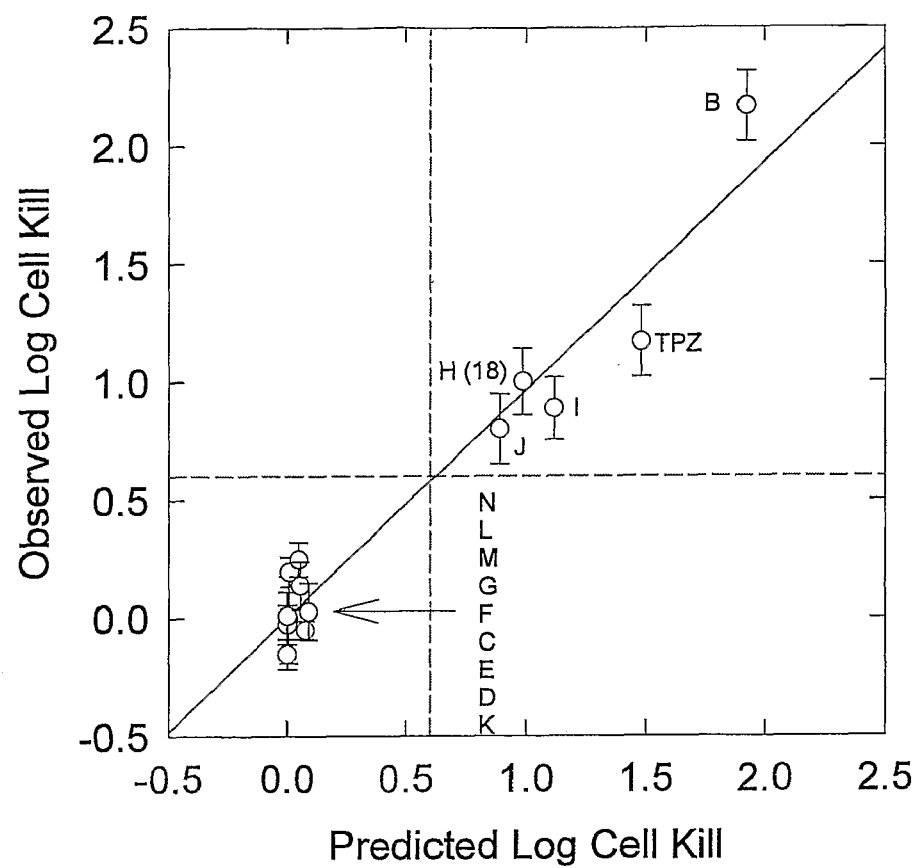

FIG. 4: Shows the predicted (PK/PD model) versus measured kill of hypoxic cells in HT29 tumors (i.e. additional kill for drug immediately after radiation, relative to radiation only).

Figure 5:
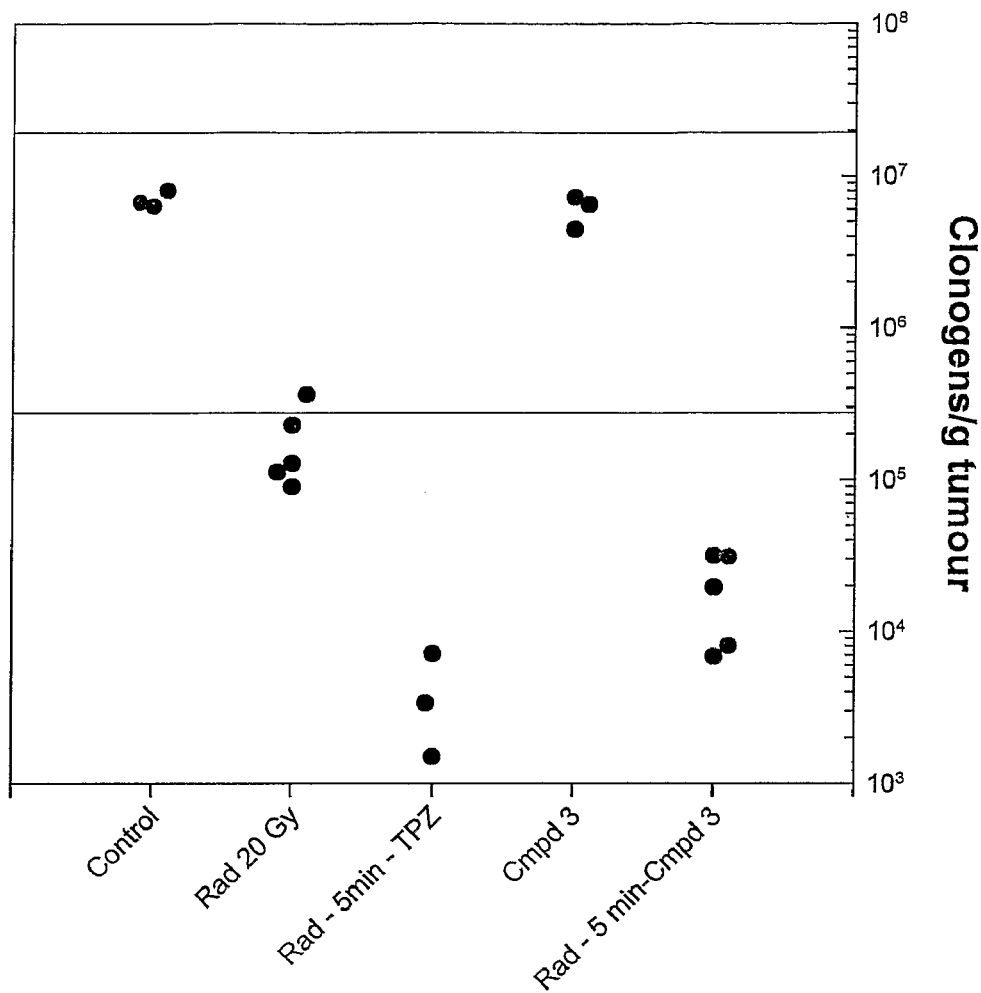

FIG. 5: Shows in vivo activity of compound 3 against hypoxic cells in HT29 tumour xenografts. Animals were treated with radiation alone (RAD, 20 Gy whole body); RAD+TPZ (316 µmol/kg); compound 3 (562 µmol/kg); RAD+compound 3 (562 µmol/kg). Tumours were excised 18 hr after treatment and clonogenic survival determined by staining colonies 14 days later. Each symbol represents a separate tumour. p<0.01 (one way ANOVA with Dunnett's test) for RAD+compound 3 and for RAD+TPZ versus RAD only. Horizontal lines are the historical means for untreated controls (upper line) and 20 Gy radiation only (lower line).

DETAILED DESCRIPTION OF THE INVENTION

Impeded extravascular transport has been previously identified as limiting the in vivo cytotoxicity and selectivity of many 1,2,4-benzotriazine-1,4-dioxides including TPZ. It is also recognised that some of the limitations of TPZ are because it is metabolised too quickly before it reaches its desired hypoxic destination. There is a complex relationship between diffusion, metabolism and in vivo activity and in order to select an improved TPZ analogue there is a need to optimize (rather than maximize) the rate of metabolism of a TPZ analogue in vivo simultaneously with the other transport and potency properties.

The inventors have now discovered a simplified but specific set of characteristics that can be used to select a TPZ analogues with therapeutic activity against hypoxic cells in human tumour xenografts, and a method by which these characteristics can be assessed without administering compounds to animals.

The determination of the desired characteristics came about by closely studying and measuring the parameters influencing and determining the extravascular transport and potency of hypoxia selective cytotoxins in vitro, PK/PD modelling, and comparison with in vivo cell killing in the HT29 excision assay the modelling and computational methods used in selecting a TPZ analogue having predicted optimised metabolism in vivo. The desired characteristics are interrelated and the limits have been carefully selected to ensure that compounds having undesirable characteristics, for example where the TPZ analogue is not sufficiently selective in its cytotoxicity under hypoxic conditions, are excluded.

The selection of the specific characteristics for a suitable TPZ analogue are as follows:

(a) a solubility greater than or about 2 mM in culture medium; and (b) an HT29 anoxic $IC_{50}$ for a 4 hr exposure to the 1,2,4-benzotriazine-1,4-dioxide of less than or about 40 µM; and (c) a hypoxic cytotoxicity ratio (HCR) greater than about 20 for the HT29 cell line; and (d) a penetration half distance (PHD) greater than or about 27 µm, and (e) the area under the plasma concentration time curve for free 1,2,4-benzotriazine-1,4-dioxide (unbound to plasma proteins), $AUC_f$ is greater than about 2 times the HT29 anoxic $IC_{50} \times t$ where $IC_{50} \times t$ is the product of concentration x exposure time for 50% inhibition of cell proliferation. (i.e. $AUC_f/(IC_{50} \times t)$ is greater than about 2);

and wherein for said 1,2,4-benzotriazine-1,4-dioxide at least one of the characteristics (a) to (e) exceeds the activity of the equivalent characteristic of Tirapazamine.

It is to be appreciated that while the characteristics have been selected to predict TPZ analogues that are active against HT29 tumours in mice, the latter cell line is representative of other human and non-human tumour cell lines in its sensitivity to TPZ [Siim et al, *Br. J. Cancer* 1996, 73, 952]. Thus it is expected that such TPZ analogues will also be active against hypoxic tumour cells in humans and other animals or at least will have an increased probability of having such activity relative to other TPZ analogues that do not meet all of the characteristics (a) to (e) above.

Although the threshold for each parameter is set at a value less favourable than the specific value determined for TPZ, these rules still make it possible to successfully predict those compounds with significant activity against hypoxic cells in human tumour xenografts in mice. For example, if a compound satisfies all of the characteristics (a) to (e) it is more likely that this compound will have significant activity against hypoxic cells in tumours.

To exemplify the invention, Table 2 provides demonstration that the above characteristics correctly identify the in vivo active compounds in the validation set of 14 compounds (cmpds A-N) that have been assayed in vivo (described in Table 1 above). It further demonstrates that the above selection rules can be successfully applied to other compounds of formula I that were not included in the initial validation set (cmpds O-U). The latter compounds were selected for in vivo testing on the basis of predicted activity according to the above selection rules. Overall, all 12 of the 12 compounds meeting the desired characteristics of selection show significant activity against hypoxic cells in HT29 tumours, whereas none of the 9 compounds failing to meet all these characteristics show significant activity. It is noteworthy that the selection rules distinguish closely related compounds such as the 6-methyl and 7-methyl regioisomers (cmpds 3 and 40) which have very similar structural and physicochemical properties. The 6-methyl analogue (3) is correctly predicted by the selection rules to be active against HT29 tumours, while the 7-methyl analogue (40) is correctly predicted to be inactive. The latter compound narrowly fails both the PHD (penetration) criterion for selection rule (c) and $AUC_f/(IC_{50} \times t)$ ratio criterion for selection rule (e).

Determination of Parameters Required for the Selection Rules (a)-(d).

(i) Determination of Solubility

Solubility is determined in laboratory culture medium (alpha minimal essential medium ($\alpha$MEM) with 5% foetal bovine serum) saturated with 5% carbon dioxide at pH 7.4, by addition of excess compound and sonication at ambient temperature for 15 minutes. Alternatively the compound is diluted from a concentrated stock solution in DMSO into culture medium to give a final DMSO concentration <1%. The mixture is centrifuged at 13,000 rpm for 6 minutes and the concentration of drug in the supernatant solution is then determined by HPLC using a standard reference solution in a suitable solvent.

(ii) Determination of Cytotoxicity

Evaluation of the Cytotoxicity of Compounds by Proliferation Assay ($IC_{50}$) Under Aerobic and Hypoxic Conditions.

Compounds representative of the invention were evaluated under both aerobic and hypoxic conditions in a proliferation assay ($IC_{50}$) using the human colon carcinoma cell line HT-29 as previously described [Hay et al, *J. Med. Chem,* 2003, 46, 169]. For each experiment, compounds were simultaneously tested under both oxic and hypoxic conditions and included TPZ as an independent internal control at the front and back of the assay. In all cases, a 8-methyl-5-nitroquinoline derivative was used as a second internal control to confirm that strict hypoxia was present during the experiment [Siim et al., *Br. J. Cancer* 1994, 70, 596]. After exposure to compounds for 4 hrs, cells were washed with fresh medium and grown for a further 5 days before staining with sulforhodamine B as described previously [Wilson et al., *J. Med. Chem.* 1989, 32, 31] and $IC_{50}$ values determined.

$IC_{50}$=The concentration of drug (in micromolar) to reduce viable cell numbers to 50% of those of control cell cultures grown on the same plate but not exposed to drug.

TABLE 2

| Cmpd | Solubility | IC50 (µM) | HCR | PHD (µM) | AUC (µM-h) | AUC/(IC50 × t) | Prediction | HT29 log kill | p value |
|---|---|---|---|---|---|---|---|---|---|
| | 2.mM | | | 20 | 27 | 2 | | | |
| A | | 8.9 | 5.15 | 70.6 | 44.4 | 148.1 | 7.2 | Active | 1.17 | <0.01 |
| B | 33 | 3.02 | 12.9 | 35.8 | 89.5 | 215.8 | 4.2 | Active | 2.165 | <0.01 |
| C | 34 | 0.09 | 0.73 | 28.5 | 25.3 | 2.7 | 0.9 | Inactive | −0.007 | ns |
| D | 35 | 2.22 | 0.55 | 13.6 | 13.1 | 0.7 | 0.3 | Inactive | −0.154 | ns |
| E | 36 | 0.49 | 9.95 | 12.0 | 24.8 | 15.6 | 0.4 | Inactive | −0.028 | ns |
| F | 40 | 38.7 | 1.08 | 34.3 | 21.6 | 3.9 | 0.9 | Inactive | 0.196 | ns |
| G | | 26 | 1.650 | 81.6 | 31.8 | 7.1 | 1.1 | Inactive | 0.248 | ns |
| H | 3 | 52 | 1.85 | 159.0 | 27.5 | 67.8 | 9.2 | Active | 1.001 | <0.01 |
| I | | 14.5 | 6.78 | 54.2 | 62.9 | 138.9 | 5.1 | Active | 0.886 | <0.01 |
| J | | 21 | 3.50 | 49.4 | 54.2 | 83.5 | 6.0 | Avtive | 0.8 | <0.05 |
| K | | 0.024 | 0.025 | 31.8 | 9.9 | 0.0 | 0.3 | Inactive | 0.009 | ns |
| L | | 0.45 | 0.050 | 154.0 | 11.0 | 3.3 | 19.2 | Inactive | −0.051 | ns |
| M | | 3.8 | 0.125 | 119.0 | 5.6 | 1.2 | 2.7 | Inactive | 0.138 | ns |
| N | | 32.4 | 0.225 | 134.0 | 25.2 | 1.6 | 1.8 | Inactive | 0.027 | ns |
| O | 5 | 42.6 | 15.5 | 24.7 | 65.2 | 195.3 | 3.1 | Active | 1.28 | <0.01 |
| P | 9 | 45.5 | 7.65 | 89.3 | 35.0 | 239.5 | 7.8 | Active | 1.84 | <0.01 |
| Q | 14 | 51.2 | 4.98 | 162.0 | 32.2 | 256.4 | 12.9 | Active | 0.53 | 0.019 |
| R | 19 | 50.3 | 2.60 | 120.6 | 51.9 | 82.4 | 7.9 | Active | 0.83 | 0.041 |
| S | 25 | 54.9 | 10.4 | 35.0 | 83.1 | 94.9 | 2.3 | Active | 0.82 | 0.049 |
| T | 30 | 48.5 | 1.33 | 307.2 | 36.6 | 55.7 | 10.5 | Active | 0.88 | <0.001 |
| U | 32 | 46.7 | 6.17 | 166.2 | 40.6 | 162.4 | 6.6 | Active | 1.66 | <0.001 |

Ability of the characteristics to be used to select in vivo active compounds from the compounds represented by Formula I. For structures of compounds A—N, refer Table 1. Other compounds are identified below. The selection rules relate to the values in columns 3, 5, 6 abd 8, and the threshold values are shown in row 2 (grey background). Compounds satisfying all the desired thresholds are shown as Active in the Prediction column. The two right hand columns show the measured activity hypoxic cells in HT29 tumours (logarithms to the base 10 of kill, additional to radiation alone) and the statistical significance of this activity relative to radiation alone (ns = not significant). The PK and in vivo activity data were determined at the MTD for some compounds or at 75% of the MTD for others.

HCR=Hypoxic cytotoxicity ratio is defined as the ratio of $IC_{50}$ values under aerobic and hypoxic condition (iii) Determination of PHD For a TPZ analogue to selectively kill hypoxic cells in vivo it must be capable of transport to the hypoxic region. Transport limitations are the result of the competition between diffusion (governed by the diffusion coefficient $D_{MCL}$ cm$^2$s$^{-1}$) and bioreductive metabolism (measured by the first order rate constant $k_{met}$ in s$^{-1}$). This competition may be summarised as the Penetration Half Distance (PHD), which is the distance into a plane one dimensional anoxic tissue region where the drug concentration falls to half of its external value, and is calculated by $$PHD = \ln(2)\sqrt{\frac{D_{MCL}}{k_{met}}}$$

where $D_{MCL}$ is the drug diffusion coefficient in HT29 MCL in units cm$^2$s$^{-1}$ and $k_{met}$ is the estimated first order rate constant for hypoxic drug metabolism in HT29 MCL at a drug concentration approximating the $C_{10}$ value in units of s$^{-1}$.

PHD for compounds representative of the invention were evaluated as described. The requirement that PHD≧27 µm ensures adequate extravascular transport by setting an upper bound on $k_{met}$ as a function of $D_{MCL}$, i.e., $k_{met}$ must be less than or equal to ⅔ $D_{MCL}\times10^5$ s$^{-1}$. The lower bound on $k_{met}$ is implied by the $IC_{50}$ and HCR conditions which ensure that the rate of metabolism under hypoxia is high enough to provide potent and selective hypoxic cell killing.

The parameters $k_{met}$ and $D_{MCL}$ can be estimated by measurement or by calculation as illustrated below., PHD=is the distance into a plane one dimensional anoxic tissue region where the drug concentration falls to half of its external value MCL=multicellular layer $D_{MCL}$=the diffusion coefficient of the drug in HT29 multicellular layers (see below)

$k_{met}$=the rate constant for bioreductive metabolism at the cell density in HT29 multicellular layers Determination of the Diffusion Coefficient in HT29 Multilayers The diffusion coefficients in HT29 MCL ($D_{MCL}$) of compounds representative of the invention were determined either by:

1. Measurement of drug diffusion in HT29 MCL (grown in culture inserts and seeded at 1×10$^6$ cells per insert and grown for 3-4 days) in a 2 chamber diffusion apparatus containing culture medium with measurement from both the donor and receiver compartments and gassing at ≧20% O2 to suppress bioreductive metabolism as described in Hicks et al (*Cancer Res.* 2003, 63, 5970-5977). Samples of medium are taken at intervals, drug concentrations determined by HPLC or LCMS and the concentration-time profile was fitted to Fick's second law of diffusion and the differential equation was solved numerically to obtain the estimate of $D_{MCL}$.

OR

2. Calculated from the logistic regression equation $$\log(D_{MCL}) = y_0 + g + d \times \log M_r + \frac{a}{1 + \exp\left(-\frac{\log P_{7.4} - x_0 + e \times HD + h \times HA}{b}\right)}$$

where a. Log $P_{7.4}$ is the base 10 logarithm of the octanol-water partition coefficient of the compound at pH 7.4 measured or calculated using the techniques described below b. HD is the number of hydrogen bond donors (which is the sum of all NH— and OH-groups)

c. HA is the number of hydrogen bond acceptors (which is the sum of all N— and O-atoms)

d. $M_r$ is the molecular weight of the non-ionised drug and a, g, d, a, $x_0$, e, h, and b are regression coefficients as outlined in the table.

| | Parameters | | | |
|---|---|---|---|---|
| | Estimate | SE | CV(%) | p |
| a | 1.0955 | 0.0746 | 6.81 | <0.0001 |
| b | 0.6452 | 0.0994 | 15.41 | <0.0001 |
| d | −0.4731 | 0.1027 | 21.71 | <0.0001 |
| e | −0.9602 | 0.0916 | 9.54 | <0.0001 |
| $x_0$ | −3.5797 | 0.3541 | 9.89 | <0.0001 |
| $y_0$ | −5.5183 | 0.2506 | 4.54 | <0.0001 |
| h | −0.3810 | 0.0490 | 12.86 | <0.0001 |

Values of the coefficient g are cell line dependent; this value has been determined as 0.3051 (SE 0.0427, CV 13.99%, p<0.001) for SiHa MCLs, and is set at zero for HT29 MCLs.

Determination of the Rate of Metabolism

The apparent first order rate constants for anoxic metabolism in HT29 cells ($k_{met}$) of compounds representative of the invention were either:

1. Estimated at the $C_{10}$ experimentally by incubating stirred single cell suspensions (typically 10 ml at 2×10$^6$/ml of HT29 cells derived by trypsinisation of multicellular spheroids) in αMEM without serum in 20 ml bottles under flowing 5% $CO_2/N_2$ for 90 min, then introducing the compound using deoxygenated DMSO stock solutions to give a range of final drug concentrations. Samples (0.5 ml) were removed at intervals (typically 5 min, 30 min, 1,2,3 hr), washed by centrifugation, and plated to determine the number of clonogenic survivors as described by Hicks et al Cancer Res. 2003 63, 5970. The concentration of compound giving 1 log of kill at 1 hr ($C_{10}$) was estimated by interpolation. Additional samples taken at the same times were centrifuged to remove cells, and supernatant stored at −80° C. for subsequent HPLC or LCMS analysis. The concentration of compound in the extracellular medium was plotted against time and the concentration closest to the $C_{10}$ was used to estimate the first order rate constant. This was scaled to MCL cell density as described in Hicks et al, *Cancer Res.* 2003, 63, 5970 to obtain $k_{met}$. Cell viability was determined with a hemocytometer at the end of drug exposure by staining with 0.4% trypan blue to ensure metabolic viability was >75%. TPZ (30 µM) was included in each experiment as a reference compound. $O_2$, in solution was measured using an OxyLite $O_2$ luminescent fiber optic probe (Oxford Optronix Ltd, UK) to ensure severe hypoxia (<0.1 µM).

OR

2. Calculated by regression against the measured one electron reduction potential E(1) to using the following equation $$\log k_{met} = -4.7220549 + 0.0106557 \times E(1) \quad (R^2=0.796)$$

where b[0] and b[1] are the regression coefficients outlined in the following table Determination of Physicochemical Parameters Physicochemical parameters of compounds representative of the invention were determined as follows.

1. log $P_{7.4}$.

The base 10 logarithm of the octanol-water partition coefficient was determined either
1. Experimentally by a modified shake flask method as described in Siim et al [Siim et al, *Biochem. Pharmacol.* 2000, 60, 969] by partitioning of drug between phosphate buffered saline and analytical grade 1-octanol at 22±2° C. with measurement of both aqueous and octanol phases by HPLC or LC/MS after equilibrium is reached.
   OR
2. By calculation using proprietary software ACD log D (Advanced Chemistry Development Inc, Toronto, Canada with inclusion of a training set of compounds for which have log $P_{7.4}$ has been measured as described above.

2. E(1)

The one-electron reduction potential (E(1)) was determined either
1. Experimentally, using pulse radiolysis [Wardman, *J. Phys. Chem. Ref. Data* 1989, 18, 1637; Anderson et al, *Brit. J. Cancer* 1996, 27, S48] performed on a Dynaray 4 (4 MeV) linear accelerator (200 ns pulse length with a custom-built optical radical detection system. E(1) values were determined in anaerobic aqueous solutions containing 2-propanol (0.1 M) buffered at pH 7.0 (10 mM phosphate) by measuring the equilibrium constant [Meisel & Czapski, *J. Phys. Chem.* 1975, 79, 1503] for the electron transfer between the radical anions of the compounds and the appropriate viologen or quinone reference standard. Data were obtained at three concentration ratios.
   OR
2. By calculation. For monosubstituted compounds, E(1) may be estimated by regression using the following equations (Hay et al., *J. Med. Chem.* 2003, 46, 169-182)

| | | | |
|---|---|---|---|
| 3-sub: E(1)/mV = −348 + 161 $\sigma_p$ | n = 5 | $r^2$ = 0.975 | F = 161 |
| 5-sub: E(1)/mV = −453 + 161$\sigma_m$ | n = 7 | $r^2$ = 0.976 | F = 160 |
| 6-sub: E(1)/mV = −454 + 282$\sigma_p$ | n = 10 | $r^2$ = 0.987 | F = 596 |
| 7-sub: E(1)/mV = −424 + 171$\sigma_p$ | n = 10 | $r^2$ = 0.933 | F = 111 |
| 8-sub: E(1)/mV = −492 + 287$\sigma_m$ | n = 10 | $r^2$ = 0.946 | F = 106 |

(iv) Determination of Free Drug AUC from Plasma Pharmacokinetics (PK)

The area under the concentration time curve for free drug ($AUC_f$) in mouse plasma at the maximum tolerated dose (MTD) was determined either experimentally or by calculation.

1. Experimental Determination of Plasma Pharmacokinetics (PK)

A. Determination of Maximum Tolerated Dose (MTD)

The compound was formulated in a suitable vehicle (e.g. 0.9% saline, 5% DMSO in 0.9% saline) and administered intraperitoneally (i.p.) as single dose to CD-1 nude mice in a dose-escalating format using 1.33-fold dose increments. The mice were weighed and observed at regular intervals and the MTD defined as the highest dose that does not cause lethality or severe morbidity or unacceptable toxicity (e.g. a weight loss of greater than 15% of the starting weight in any individual animal) in a group of 3-6 mice.

B. Plasma Pharmacokinetics (PK)

The compound was administered to CD-1 nude mice in a suitable formulation as a single dose (i.p.) at the MTD. Blood samples were collected by retro-orbital sinus bleed or cardiac puncture after which the mouse was culled, or by serial bleeding from the tail vein. Typical time points were 15, 30, 60, and 120 min after administration. Blood was collected in a heparinised container and centrifuged to collect the plasma. The plasma concentration of the compound was determined by HPLC or LCMS using suitable sample preparation and analytical methods. Calibration was done with internal or external standards. The area under the concentration-time curve (AUC) for total (free plus bound) drug was calculated using the linear/log trapezoidal rule and extrapolation to infinity OR standard non-compartmental (PK) modelling.

C. Determination of Plasma Protein Binding

Plasma protein binding was measured by the determination of the free fraction (FF) by equilibrium dialysis at 37° C. in 50% (v/v) mouse plasma in phosphate-buffered saline (pH 7.4), using a single drug concentration at or near the observed or extrapolated maximum concentration in plasma ($C_{max}$). Compound concentrations after dialysis were determined by HPLC or LCMS. The plasma protein FF was then used to estimate binding in 100% mouse plasma using the relationship:

$$FF(100\% \text{ plasma}) = 0.5\, FF(50\% \text{ plasma})$$

D. Determination of the AUC for Free Drug

The AUC for the free drug ($AUC_f$) was estimated using the equation:

$$AUC_f = FF(100\% \text{ plasma}) \times AUC$$

2. Calculation of $AUC_f$ $AUC_f$ for the compound administered as a single dose (i.p.) to CD-1 nude mice at the MTD can be estimated using the following regression equation:

$$Log_{10}(AUC_f) = a + b \times \log P_{neutral} + c \times log_{10}(IC_{50}) + d \times log_{10}(HCR) + e \times log_{10}(D_{MCL}) + f \times log_{10}(k_{met}) + g \times (\log P_{neutral})^2$$

where the coefficients are described in the following table:

| | Coefficient | Std. Error | CV % | P |
|---|---|---|---|---|
| a | 0.3810 | 0.3573 | 93.7795 | 0.3091 |
| b | −0.1411 | 0.1208 | 85.6130 | 0.2676 |
| c | 1.3007 | 0.1794 | 13.7926 | <0.0001 |
| d | 0.9457 | 0.1771 | 18.7269 | 0.0002 |
| e | 0.8940 | 0.2069 | 23.1432 | 0.0012 |
| f | −0.1739 | 0.1937 | 111.3859 | 0.3885 |
| g | −0.3068 | 0.0728 | 23.7288 | 0.0015 |

N=18 $R^2$=0.9556 SE=0.1877 F=39.4382 P<0.0001

Methods for Preparing Compounds of Formula I of the Invention.

Nucleophilic displacement of 1 with N,N-dimethyethylenediamine gave 1-oxide 2 that underwent selective aromatic N-oxidation under acidic conditions to give 1,4-dioxide 3 (Scheme 1).

Scheme 1

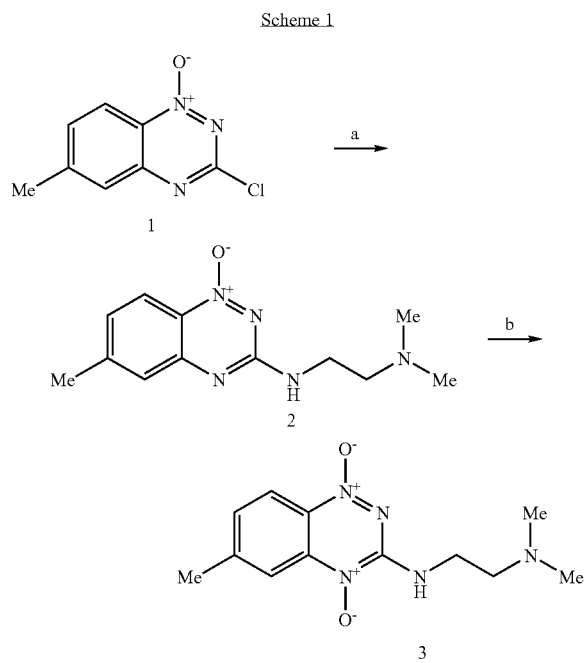

Reagents:
a) N,N-dimethyethylenediamine, DME;
b) CF₃CO₃H, CF₃CO₂H, DCM.

Similarly, reaction of chloride 1 with 4-(3-aminopropyl) morpholine gave 1-oxide 4 which was oxidized to 1,4-dioxide 5 (Scheme 2).

Scheme 2

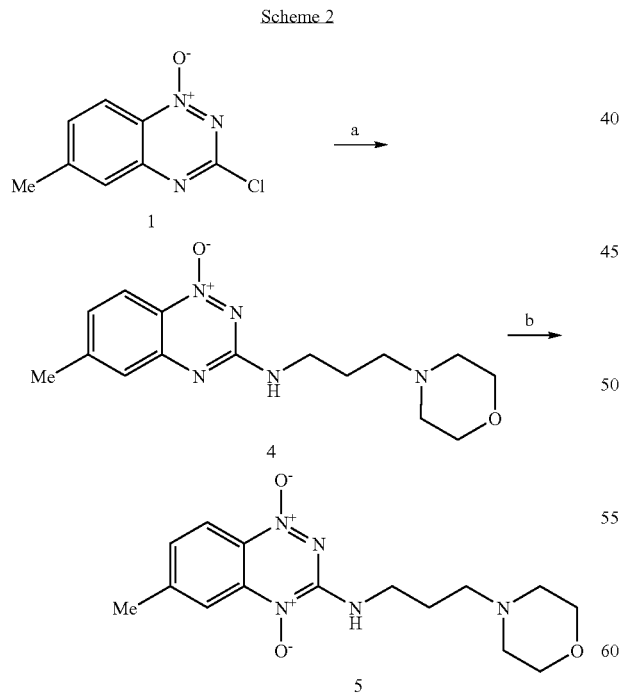

Reagents:
a) 4-(3-aminopropyl)morpholine, DME;
b) CF₃CO₃H, CF₃CO₂H, DCM.

Diazotisation of amine 6 (Hay et. al., *J. Med. Chem.* 2003, 46, 169) in trifluoroacetic acid and chlorination of the intermediate phenol gave chloride 7 (Scheme 3). Nucleophilic displacement of chloride 7 with N,N-dimethylethylenediamine gave the 1-oxide 8 that was oxidised to the corresponding 1,4-dioxide 9.

Scheme 3

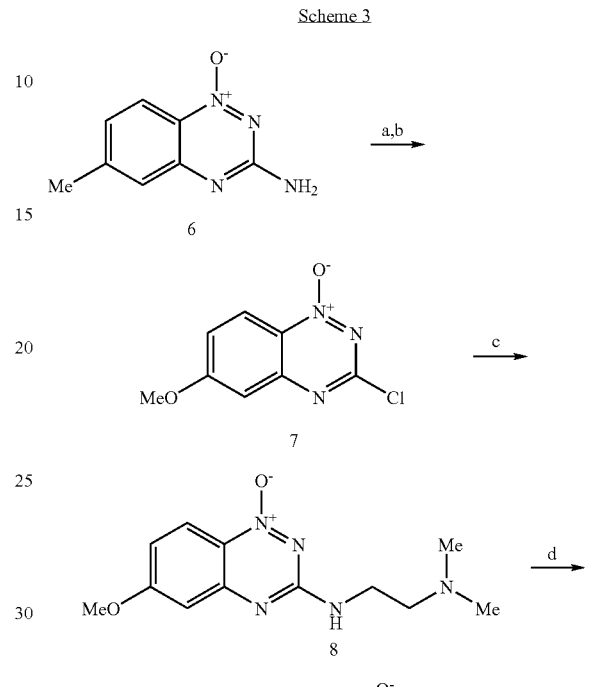

Reagents:
a) NaNO₂, TFA;
b) POCl₃, DMF;
c) NH₂CH₂CH₂NMe₂, DME;
d) CF₃CO₃H, CF₃CO₂H, DCM.

Diazotisation of amine 10 (Hay et. al., *J. Med. Chem.* 2003, 46, 169) in trifluoroacetic acid and chlorination of the intermediate phenol gave chloride 11 (Scheme 4). Nucleophilic displacement of chloride 11 with N,N-dimethylethylenediamine gave the 1-oxide 12. Displacement of fluoride 12 with the anion of 2-methoxyethanol gave 1-oxide 13, which was oxidised to the corresponding 1,4-dioxide 14.

Scheme 4

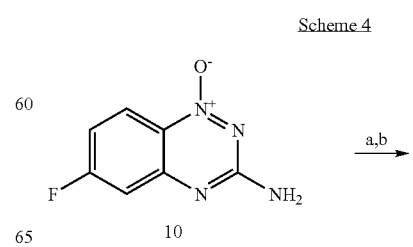

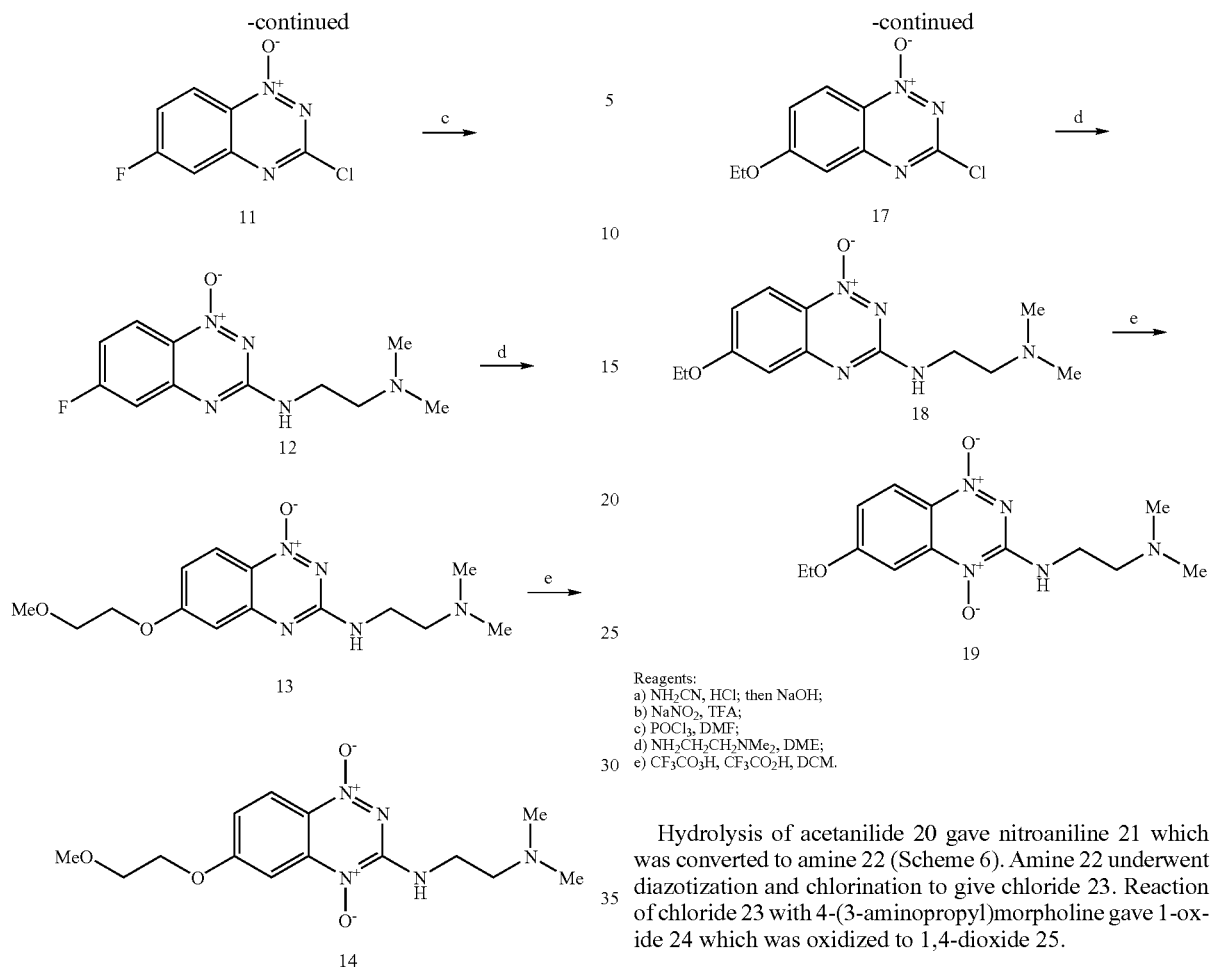

Reagents:
a) NH$_2$CN, HCl; then NaOH;
b) NaNO$_2$, TFA;
c) POCl$_3$, DMF;
d) NH$_2$CH$_2$CH$_2$NMe$_2$, DME;
e) CF$_3$CO$_3$H, CF$_3$CO$_2$H, DCM.

Hydrolysis of acetanilide 20 gave nitroaniline 21 which was converted to amine 22 (Scheme 6). Amine 22 underwent diazotization and chlorination to give chloride 23. Reaction of chloride 23 with 4-(3-aminopropyl)morpholine gave 1-oxide 24 which was oxidized to 1,4-dioxide 25.

Reagents:
a) NaNO$_2$, TFA;
b) POCl$_3$, DMF;
c) NH$_2$CH$_2$CH$_2$NMe$_2$, DME;
d) NaH, 2-methoxyethanol, THF;
e) CF$_3$CO$_3$H, CF$_3$CO$_2$H, DCM.

Condensation of nitroaniline 15 with cyanamide and cyclisation under basic conditions gave amine 16, which was converted to the chloride 17 (Scheme 5). Reaction of 17 with N,N-dimethylethylenediamine gave the 1-oxide 18, which was oxidised to the corresponding 1,4-dioxide 19.

Scheme 5

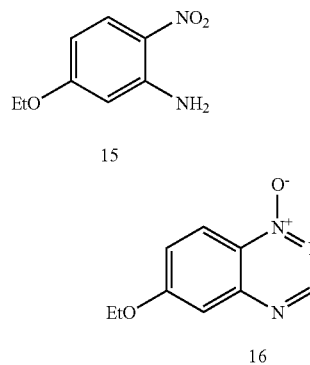

Scheme 6

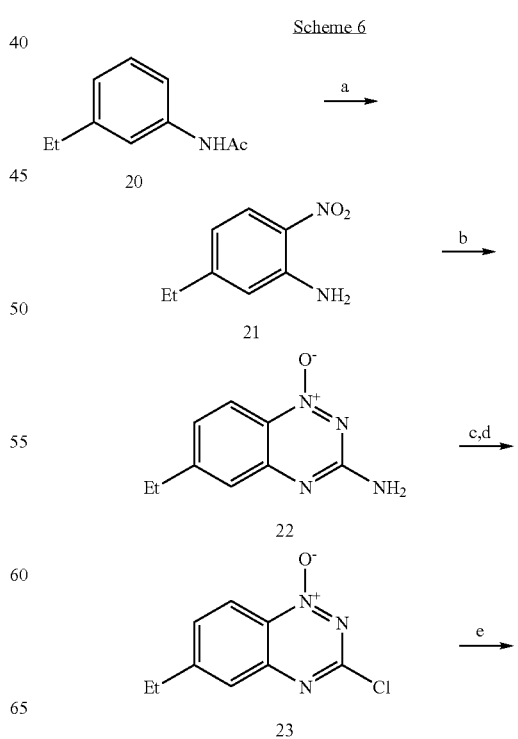

-continued

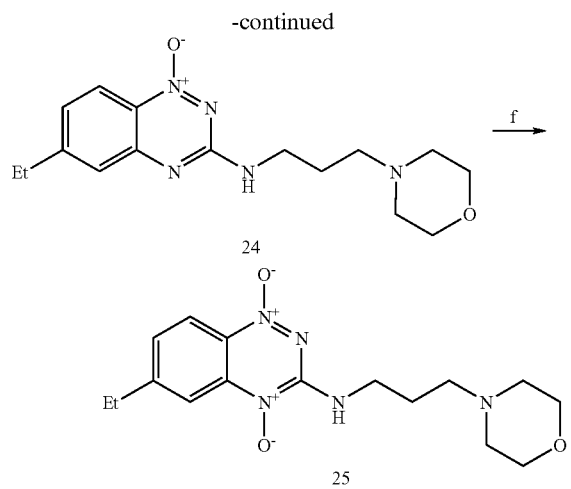

Reagents:
a) 5 M HCl;
b) NH₂CN, HCl; then NaOH;
c) NaNO₂, TFA;
d) POCl₃, DMF;
e) NH₂CH₂CH₂CH₂NMORPH, Et₃N, DME;
f) CF₃CO₃H, CF₃CO₂H, DCM.

Diazotization of the amine 26 and chlorination of the intermediate phenol gave chloride 27 (Scheme 7). Stille reaction of chloride 27 with tetraethyltin in the presence of a palladium catalyst gave compound 28. Reaction of 28 with the anion of N,N-dimethylethanolamine gave the 1-oxide 29, which was oxidized to the 1,4-dioxide 30.

Scheme 7

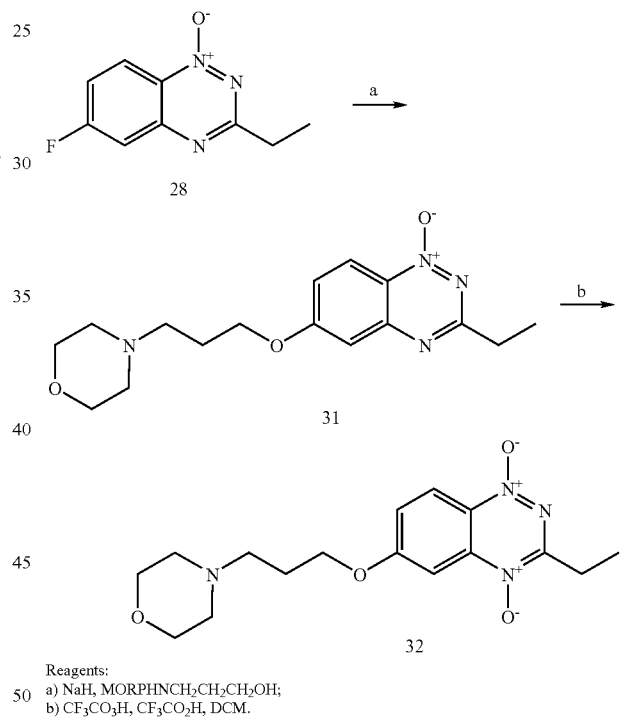

-continued

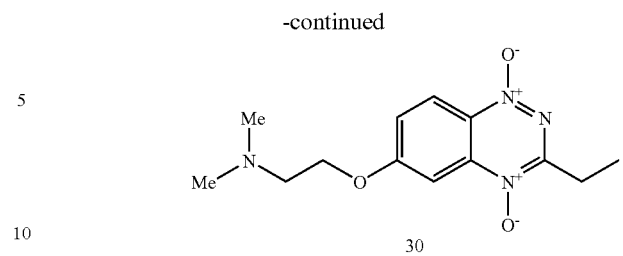

Reagents:
a) NaNO₂, TFA;
b) POCl₃, DMF;
c) Et₄Sn, Pd(PPh₃)₄, DME;
d) Na, Me₂NCH₂CH₂OH;
e) CF₃CO₃H, CF₃CO₂H, DCM.

Similarly, reaction of fluoride 28 with the anion of 3-(4-morpholinyl)propanol gave 1-oxide 31, which was oxidized to 1,4-dioxide 32 (Scheme 8).

Scheme 8

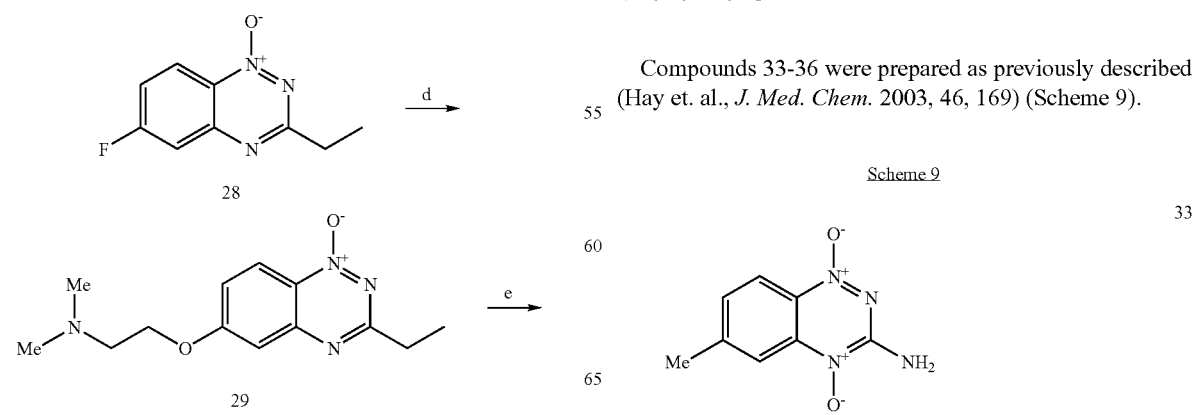

Reagents:
a) NaH, MORPHNCH₂CH₂CH₂OH;
b) CF₃CO₃H, CF₃CO₂H, DCM.

Compounds 33-36 were prepared as previously described (Hay et. al., *J. Med. Chem.* 2003, 46, 169) (Scheme 9).

Scheme 9

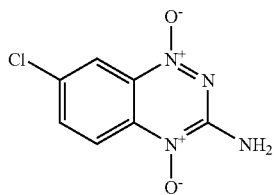

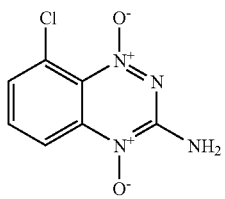

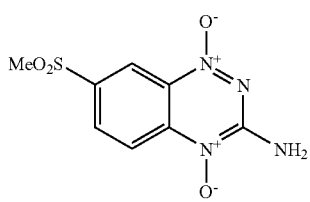

Diazotization of the amine 37 (Hay et. al., *J. Med. Chem.* 2003, 46, 169) and chlorination of the intermediate phenol gave chloride 38 (Scheme 10). Nucleophilic displacement of 38 with N,N-dimethyethylenediamine gave 1-oxide 39 that underwent selective aromatic N-oxidation under acidic conditions to give 1,4-dioxide 40.

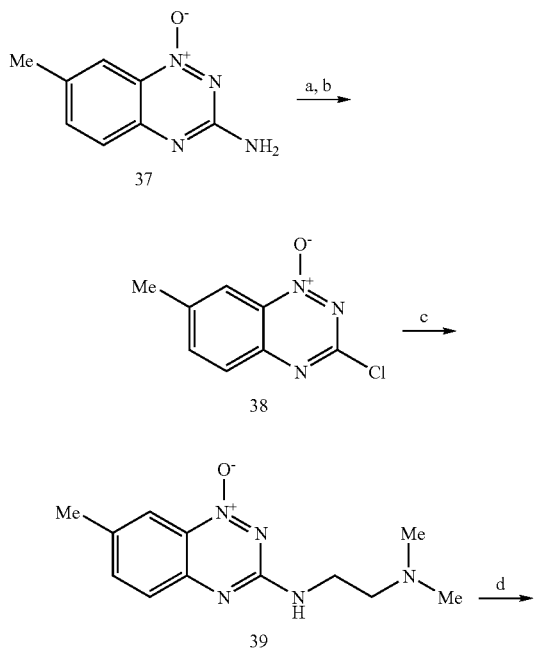

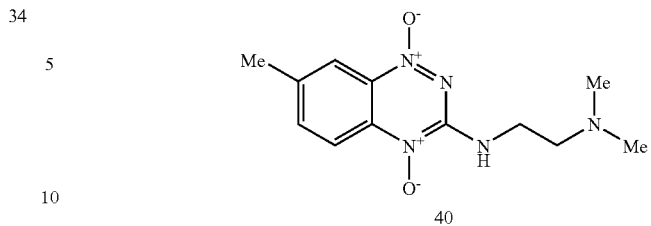

Reagents:
a) $NaNO_2$, TFA;
b) $POCl_3$, DMF;
c) $NH_2CH_2CH_2NMe_2$, DME;
d) $CF_3CO_3H$, $CF_3CO_2H$, DCM.

EXAMPLES OF THE COMPOUNDS OF THE INVENTION

The following examples are representative of the invention and the detailed methods for preparing them, however, the scope of the invention is not to be taken as being limited to these examples.

Analyses were carried out in the Microchemical Laboratory, University of Otago, Dunedin, NZ. Melting points were determined on an Electrothermal 2300 Melting Point Apparatus. NMR spectra were obtained on a Bruker Avance 400 spectrometer at 400 MHz for $^1$H and 100 MHz for $^{13}$C spectra. Spectra were obtained in $CDCl_3$ unless otherwise specified, and are referenced to $Me_4Si$. Chemical shifts and coupling constants were recorded in units of ppm and Hz, respectively. Assignments were determined using COSY, HSQC, and HMBC two-dimensional experiments. Mass spectra were determined on a VG-70SE mass spectrometer using an ionizing potential of 70 eV at a nominal resolution of 1000. High-resolution spectra were obtained at of 70 eV at a nominal resolution of 1000. High-resolution spectra were obtained at nominal resolutions of 3000, 5000, or 10000 as appropriate. All spectra were obtained as electron impact (EI) using PFK as the reference unless otherwise stated. Solutions in organic solvents were dried with anhydrous $Na_2SO_4$. Solvents were evaporated under reduced pressure on a rotary evaporator. Thin-layer chromatography was carried out on aluminum-backed silica gel plates (Merck 60 $F_{254}$) with visualization of components by UV light (254 nm) or exposure to $I_2$. Column chromatography was carried out on silica gel, (Merck 230-400 mesh). Basic compounds were formulated as hydrochloride salts for solubility testing, formulation and all biological assays. All compounds designated for biological testing were analysed at >99% purity by reverse phase HPLC using a Philips PU4100 liquid chromatograph, a Phenomenex BondClone 10-C18 stainless steel column (300 mm×3.9 mm i.d.) and a Philips PU4120 diode array detector. Chromatograms were run using various gradients of aqueous (1 M $NaH_2PO_4$, 0.75 M heptanesulfonic acid, 0.5 M dibutylammonium phosphate, and MilliQ water in a 1:1:1:97 ratio) and organic (80% MeOH/MilliQ water) phases. DCM refers to dichloromethane; DME refers to 1,2-dimethoxyethane, DMF refers to dry dimethylformamide; ether refers to diethyl ether; EtOAc refers to ethyl acetate; EtOH refers to ethanol; MeOH refers to methanol; pet ether refers to petroleum ether,

Example 1

$N^1,N^1$-Dimethyl-$N^2$-(6-methyl-1,4-dioxido-1,2,4-benzotriazin-3-yl)-1,2-ethanediamine (3)

$N^1,N^1$-Dimethyl-$N^2$-(6-methyl-1-oxido-1,2,4-benzotriazin-3-yl)-1,2-ethanediamine (2). N,N-Dimethylethanediamine (705 µL, 6.6 mmol) was added to a stirred solution of chloride 1 (518 mg, 2.7 mmol) in DME (50 mL) and the solution stirred at reflux temperature for 2 h. The solution was cooled, the solvent evaporated and the residue partitioned between dilute aqueous $NH_3$ (100 mL) and DCM (100 mL). The organic fraction was dried and the solvent evaporated. The residue was purified by chromatography, eluting with a gradient (0-10%) of MeOH/DCM, to give 1-oxide 2 (603 mg, 92%) as a yellow solid, mp (MeOH/EtOAc) 143-145° C.; $^1$H NMR δ 8.11 (d, J=8.8 Hz, 1 H, H-8), 7.35 (d, J=1.7 Hz, 1 H, H-5), 7.07 (dd, J=8.8, 1.7 Hz, 1 H, H-7), 5.89 (br s, 1 H, NH), 3.50-3.56 (m, 2 H, $CH_2N$), 2.52-2.56 (m, 2 H, $CH_2N$), 2.45 (s, 3 H, $CH_3$), 2.26 [s, 6 H, $N(CH_3)_2$]; $^{13}$C NMR δ 159.2, 149.1, 146.9, 129.2, 126.9, 125.3, 120.1, 57.5, 45.1 (2), 38.7, 22.0. Anal. calcd for $C_{12}H_{17}N_5O$: C, 58.3; H, 6.9; N, 28.3; found C, 58.5: H, 7.1; N, 28.6%.

$N^1,N^1$-Dimethyl-$N^2$-(6-methyl-1,4-dioxido-1,2,4-benzotriazin-3-yl)-1,2-ethanediamine (3). Hydrogen peroxide (70%, 1.1 mL, ca. 22.9 mmol) was added dropwise to a stirred solution of trifluoroacetic anhydride (3.2 mL, 22.9 mmol) in DCM (20 mL) at 5° C. The mixture was stirred at 5° C. for 5 min, warmed to 20° C., stirred for 10 min, and cooled to 5° C. The mixture was added to a stirred solution of 1-oxide 2 (566 mg, 2.3 mmol) and trifluoroacetic acid (353 µL, 4.6 mmol) in $CHCl_3$ (20 mL) at 5° C. and the mixture stirred at 20° C. for 16 h. The solution was carefully diluted with dilute aqueous $NH_3$ solution (20 mL) and the mixture extracted with $CHCl_3$ (5×50 mL). The organic fraction was dried and the solvent evaporated. The residue was purified by chromatography, eluting with a gradient (0-10%) of MeOH/DCM, to give 1,4-dioxide 3 (207 mg, 34%) as a red solid, mp (MeOH/EtOAc) 187-189° C.; $^1$H NMR δ 8.19 (d, J=9.0 Hz, 1 H, H-8), 8.05 (d, J=1.7 Hz, 1 H, H-5), 7.44. (br s, 1 H, NH), 7.29 (dd, J=9.0, 1.7 Hz, 1 H, H-7), 3.58-3.64 (m, 2 H, $CH_2N$), 2.57-2.61 (m, 2 H, $CH_2N$), 2.56 (s, 3 H, $CH_3$), 2.28 [s, 6 H, $(CH_3)_2$]; $^{13}$C NMR δ 149.9, 148.0, 138.2, 129.3, 128.8, 121.4, 116.0, 57.4, 45.2 (2), 38.7, 22.3. Anal. Calcd for $C_{12}H_{17}N_5O_2$: C, 54.7; H, 6.5; N, 26.6. Found: C, 54.3: H, 6.7; N, 26.8%.

Example 2

6-Methyl-N-[3-(4-morpholinyl)propyl]-1,2,4-benzotriazin-3-amine 1,4-Dioxide (5)

6-Methyl-N-[3-(4-morpholinyl)propyl]-1,2,4-benzotriazin-3-amine 1-Oxide (4). 3-(1-Morpholinyl)propylamine (2.37 mL, 16.2 mmol) was added to a stirred solution of chloride 1 (1.06 g, 5.4 mmol) in DME (80 mL) and the solution stirred at reflux temperature for 6 h. The solution was cooled, the solvent evaporated and the residue partitioned between dilute aqueous $NH_3$ (150 mL) and DCM (150 mL). The organic fraction was dried and the solvent evaporated. The residue was purified by chromatography, eluting with a gradient (0-10%) of MeOH/DCM, to give 1-oxide 4 (1.50 g, 95%) as a yellow powder, mp (EtOAc) 131-132° C.; $^1$H NMR δ 8.13 (d, J=8.8 Hz, 1 H, H-8), 7.36 (br s, 1 H, H-5), 7.09 (dd, J=8.8, 1.6 Hz, 1 H, H-7), 6.25 (br s, 1 H, NH), 3.75-3.77 (m, 4 H, 2×$CH_2O$), 3.57-3.62 (m, 2 H, $CH_2N$), 2.46-2.53 (m, 9 H, 3×$CH_2N$, $CH_3$), 1.81-1.87 (m, 2 H, $CH_2$); $^{13}$C NMR δ 159.2, 146.9, 1440, 129.5, 126.9, 125.4, 120.2, 67.0 (2), 57.3, 53.8 (2), 40.9, 25.2, 22.0. Anal. Calcd for $C_{15}H_{21}N_5O_2$: C, 59.4; H, 7.0; N, 23.1. Found: C, 59.5; H, 7.0; N, 22.8%.

6-Methyl-N-[3-(4-morpholinyl)propyl]-1,2,4-benzotriazin-3-amine 1,4-Dioxide (5). $H_2O_2$ (ca. 70%, 3.0 mL, 59.2 mmol) was added dropwise to a stirred solution of trifluoroacetic anhydride (8.4 mL, 59.2 mmol) in DCM (50 mL) at 5° C. The solution was stirred at 5° C. for 5 min, warmed to 20° C. for 10 min, then cooled to 5° C. and added to a stirred solution of 1-oxide 4 (1.48 g, 5.1 mmol) and trifluoroacetic acid (2.2 mL, 28.0 mmol) in $CHCl_3$ (20 mL) at 5° C. The solution was stirred at 5° C. for 16 h, diluted with dilute aqueous $NH_3$ solution (10 mL) and extracted with $CHCl_3$ (4×50 mL). The combined organic fraction was dried and the solvent evaporated. The residue was chromatographed, eluting with a gradient (0-10%) of MeOH/DCM, to give 1,4-dioxide 5 (529 mg, 32%) as a red solid, mp (MeOH/EtOAc) 155-158° C.; $^1$H NMR δ 8.54 (brs, 1 H, NH), 8.19 (d, J=9.0 Hz, 1 H, H-8), 8.08 (brs, 1 H, H-5), 7.38 (dd, J=9.0, 1.5 Hz, 1 H, H-7), 3.82-3.85 (m, 4 H, 2×$CH_2O$), 3.66-3.70 (m, 2 H, $CH_2N$), 2.55-2.59 (m, 5 H, $CH_2N$, $CH_3$), 2.49-2.54 (m, 4 H, 2×$CH_2N$), 1.85-191 (m, 2 H, $CH_2$); $^{13}$C NMR δ 150.0, 147.9, 138.3, 129.1, 128.7, 121.4, 116.1, 66.9 (2), 57.8, 53.9 (2), 41.7, 24.7, 22.3. Anal. Calcd for $C_{15}H_{21}N_5O_3$¼$CH_3OH$: C, 56.0; H, 6.8; N, 21.4. Found: C, 55.9; H, 6.7; N, 21.0%.

Example 3

$N^1$-(6-Methoxy-1,4-dioxido-1,2,4-benzotriazin-3-yl)-$N^2,N^2$-dimethyl-1,2-ethanediamine (9)

3-Chloro-6-methoxy-1,2,4-benzotriazine 1-Oxide (7). Sodium nitrite (7.14 g, 103.4 mmol) was added in portions to a stirred solution of 6-methoxy-1,2,4-benzotriazin-3-amine 1-oxide 6 [Hay et. al., *J. Med. Chem.* 2003, 46, 169] (9.94 g, 51.7 mmol) in trifluoroacetic acid (50 mL) at 5° C. and the solution stirred at 20° C. for 1 h. The solution was poured into ice/water, filtered, washed with water (2×50 mL) and dried. The solid was suspended in $POCl_3$ (80 mL), DMF (2 drops) added, and the mixture stirred at 100° C. for 3 h. The solution was poured into ice/water, stirred for 20 minutes and filtered. The solid was dissolved in DCM (150 mL), dried, and the solvent evaporated. The residue was purified by chromatography, eluting with 5% EtOAc/DCM, to give chloride 7 (7.42 g, 68%) as a pale yellow solid, mp (EtOAc/DCM) 196-199° C.; $^1$H NMR δ 8.30 (d, J=9.6 Hz, 1 H, H-8), 7.32 (dd, J=9.6, 2.7 Hz, 1 H, H-7), 7.19 (d, J=2.7 Hz, 1 H, H-5), 4.01 (s, 3 H, $OCH_3$); $^{13}$C NMR δ 166.3, 157.8, 150.2, 128.9, 123.9, 121.9, 105.7, 56.5. Anal. Calcd for $C_8H_6ClN_3O_2$: C, 45.4; H, 2.9; N, 19.9; Cl, 16.8. Found: C, 45.2; H, 2.6; N, 19.9; Cl, 16.9%.

$N^1$-(6-Methoxy-1-oxido-1,2,4-benzotriazin-3-yl)-$N^2,N^2$-dimethyl-1,2-ethanediamine (8). N,N-Dimethyl-1,2-ethanediamine (1.33 mL, 12.1 mmol) was added to a stirred solution of chloride 7 (0.85 g, 4.04 mmol) in DME (50 mL) and the solution stirred at reflux temperature for 16 h. The solvent was evaporated and the residue was partitioned between DCM (100 mL) and dilute aqueous $NH_3$ (50 mL). The organic fraction was dried and the solvent evaporated. The residue was purified by chromatography, eluting with a gradient (0-5%) of MeOH/DCM, to give amine 8 (0.72 g, 68%) which was dissolved in HCl-saturated MeOH, the solvent evaporated and the residue crystallized as a tan solid, mp (MeOH/EtOAc) 236-239° C.; $^1$H NMR [$(CD_3)_2SO$] δ 10.68 (br s, 1 H, $NH^+Cl^-$), 8.07 (d, J=9.3 Hz, 1 H, H-8), 8.03 (br s, 1 H, NH), 6.95-6.99 (m, 2 H, H-5, H-7), 3.92 (s, 3 H, OCH$_3$), 3.70-3.76 (m, 2 H, CH$_2$N), 3.30-3.35 (m, 2 H, CH$_2$N), 2.81 [d, J=4.9 Hz, 6 H, N(CH$_3$)$_2$]; $^{13}$C NMR [(CD$_3$)$_2$SO] δ 164.9, 159.0, 150.4, 125.4, 121.6, 117.3, 104.3, 55.2, 55.0, 42.3 (2), 35.8. Anal. Calcd for C$_{12}$H$_{18}$ClN$_5$O$_2$: C, 48.1; H, 6.1; N, 23.4; Cl, 11.8. Found: C, 48.3; H, 6.1; N, 23.6; Cl, 11.9%.

N$^1$-(6-Methoxy-1,4-dioxido-1,2,4-benzotriazin-3-yl)-N$^2$,N$^2$-dimethyl-1,2-ethanediamine (9). Hydrogen peroxide (70%; 1.1 mL, ca. 22.6 mmol) was added dropwise to a stirred solution of trifluoroacetic anhydride (3.2 mL, 22.6 mmol) in DCM (15 mL) at 5° C. The solution was stirred at 5° C. for 5 min, warmed to 20° C. for 10 min, then cooled to 5° C. and added to a stirred solution of 1-oxide 8 (597 mg, 2.3 mmol) and trifluoroacetic acid (350 μL, 4.5 mmol) in CHCl$_3$ (15 mL) at 5° C. The solution was stirred at 5° C. for 4 h, diluted with dilute aqueous NH$_3$ solution (10 mL) and extracted with CHCl$_3$ (4×50 mL). The combined organic fraction was dried and the solvent evaporated. The residue was purified by chromatography, eluting with a gradient (0-10%) of MeOH/DCM, to give 1,4-dioxide 9 (424 mg, 67%) as a red solid which was dissolved in HCl saturated MeOH, the solvent evaporated and the residue crystallized to give the hydrochloride, mp (MeOH/EtOAc) 170-174° C.; $^1$H NMR [(CD$_3$)$_2$SO] δ 10.57 (brs, 1 H, NH$^+$Cl$^-$), 8.45 (brs, 1 H, NH), 8.17 (d, J=9.6 Hz, 1 H, H-8), 7.39 (d, J=2.6 Hz, 1 H, H-5), 7.22 (dd, J=9.6, 2.6 Hz, 1 H, H-7), 4.01 (s, 3 H, OCH$_3$), 3.78-3.82 (m, 2 H, CH$_2$N), 3.33-3.37 (m, 2 H, CH$_2$N), 2.82 [d, J=4.5 Hz, 6 H, N(CH$_3$)$_2$]; $^{13}$C NMR [(CD$_3$)$_2$SO] δ 165.6, 150.1, 139.7, 125.7, 123.4, 119.4, 92.5, 56.8, 54.9, 42.3 (2), 36.0. Anal. Calcd for C$_{12}$H$_{18}$ClN$_5$O$_3$.1½H$_2$O: C, 42.1; H, 6.2; N, 20.4. Found: C, 42.0; H, 5.9; N, 20.0%.

Example 4

N$^1$-[6-(2-Methoxyethoxy)-1,4-dioxido-1,2,4-benzotriazin-3-yl]-N$^2$,N$^2$-dimethyl-1,2-ethanediamine (14)

3-Chloro-6-fluoro-1,2,4-benzotriazine 1-Oxide (11). NaNO$_2$ (4.26 g, 61.7 mmol) was added in small portions to a stirred solution of amine 10 [Hay et. al., *J. Med. Chem.* 2003, 46, 169] (5.56 g, 30.9 mmol) in trifluoroacetic acid (60 mL) at 5° C. and the solution stirred at 20° C. for 3 h. The solution was poured into ice/water, stirred 30 minutes, filtered, washed with water (3×30 mL) and dried. The solid was suspended in POCl$_3$ (80 mL) and DMF (0.5 mL) and stirred at 100° C. for 1 h. The solution was cooled, poured into ice/water, stirred for 30 minutes, filtered, washed with water (3×30 mL) and dried. The solid was suspended in DCM (150 mL), dried and the solvent evaporated. The residue was purified by chromatography, eluting with 5% EtOAc/DCM, to give chloride 11 (2.78 g, 45%) as a pale yellow solid, mp (EtOAc/DCM) 166-168° C.; $^1$H NMR δ 8.45 (dd, J=9.5, 5.3 Hz, 1 H, H-8), 7.61 (dd, J=8.3, 2.6 Hz, 1 H, H-5), 7.45-7.52 (m, 1 H, H-7); $^{13}$C NMR δ 167.1 (q, J=264 Hz), 158.4, 149.2, 131.0, 123.4 (d, J=11 Hz), 120.1 (d, J=26 Hz), 112.9 (d, J=23 Hz). Anal. Calcd for C$_7$H$_3$ClFN$_3$O: C, 42.1; H, 1.5; N, 21.1; Cl, 17.8. Found: C, 42.4; H, 1.6; N, 21.2; Cl, 17.8%.

N$^1$-(6-Fluoro-1-oxido-1,2,4-benzotriazin-3-yl)-N$^2$,N$^2$-dimethyl-1,2-ethanediamine (12). N,N-Dimethylethanediamine (1.60 mL, 14.6 mmol) was added to a stirred solution of chloride 11 (1.17 g, 5.9 mmol) in DME (100 mL) and the solution stirred at reflux temperature for 2 h. The solution was cooled, the solvent evaporated and the residue partitioned between dilute aqueous NH$_3$ (100 mL) and DCM (100 mL). The organic fraction was dried and the solvent evaporated. The residue was purified by chromatography, eluting with a gradient (0-10%) MeOH/DCM, to give 1-oxide 12 (1.19 g, 81%) as a yellow solid, mp (MeOH/EtOAc) 157-159° C.; $^1$H NMR δ 8.26 (dd, J=9.4, 5.7 Hz, 1 H, H-8), 7.19 (br d, J=8.0 Hz, 1 H, H-5), 6.99 (ddd, J=9.4, 8.0, 2.6 Hz, 1 H, H-7), 6.05 (br s, 1 H, NH), 3.52-3.56 (m, 2 H, CH$_2$N), 2.56 (dd, J=6.1, 5.9 Hz, 2 H, CH$_2$N), 2.27 [s, 6 H, N(CH$_3$)$_2$]; $^{13}$C NMR δ 166.9 (d, J=258 Hz), 159.5, 150.9 (d, J=15 Hz), 128.1, 123.4 (d, J=11 Hz), 114.5 (d, J=26 Hz), 110.4 (d, J=21 Hz), 57.4, 45.1 (2), 38.7. Anal. Calcd for C$_{11}$H$_{14}$N$_5$O: C, 52.6; H, 5.6; N, 27.9. Found: C, 52.3; H, 5.6; N, 28.1%.

N$^1$-[6-(2-Methoxyethoxy)-1-oxido-1,2,4-benzotriazin-3-yl]-N$^2$,N$^2$-dimethyl-1,2-ethanediamine (13). NaH (66 mg, 60% dispersion in oil, 1.7 mmol) was added to a stirred solution of fluoride 12 (261 mg, 1.0 mmol) and 2-methoxyethanol (0.12 mL, 1.6 mmol) in THF (10 mL) at 20° C. and the mixture stirred at reflux temperature for 2 h. More NaH (66 mg, 1.6 mmol) and 2-methoxyethanol (0.12 mL, 1.6 mmol) were added and the mixture stirred at reflux temperature for 16 h. The mixture was cooled to 20° C. and carefully quenched with water (5 mL). The solvent was evaporated and the residue partitioned between DCM (50 mL) and water (50 mL). The organic fraction was dried and the solvent evaporated. The residue was purified by chromatography, eluting with a gradient (0-10%) of MeOH/DCM, to give 1-oxide 13 (296 mg, 93%) as a yellow solid, mp (MeOH/EtOAc) 139-141° C.; $^1$H NMR δ 8.14 (d, J=9.4 Hz, 1 H, H-8), 6.91 (dd, J=9.4, 2.6 Hz, 1 H, H-7), 6.84 (d, J=2.6 Hz, 1 H, H-5), 5.91 (br s, 1 H, NH), 4.20-4.23 (m, 2 H, CH$_2$O), 3.71-3.74 (m, 2 H, CH$_2$O), 3.51-3.56 (m, 2 H, CH$_2$N), 3.46 (s, 3 H, OCH$_3$), 2.55 (br dd, J=6.0, 5.9 Hz, 2 H, CH$_2$N), 2.28 [s, 6 H, (CH$_3$)$_2$]; $^{13}$C NMR δ 164.6, 159.6, 151.4, 126.1, 122.1, 118.0, 104.6, 70.5, 68.0, 59.3, 57.5, 45.1 (2), 38.7. Anal. Calcd for C$_{14}$H$_{21}$N$_5$O$_3$: C, 54.7; H, 6.9; N, 22.8. Found: C, 54.5; H, 6.7; N, 22.7%.

N$^1$-[6-(2-Methoxyethoxy)-1,4-dioxido-1,2,4-benzotriazin-3-yl]-N$^2$,N$^2$-dimethyl-1,2-ethanediamine (14). Hydrogen peroxide (70%, 0.44 mL, ca. 8.7 mmol) was added dropwise to a stirred solution of trifluoroacetic anhydride (1.23 mL, 8.7 mmol) in DCM (20 mL) at 5° C. The mixture was stirred at 5° C. for 5 min, warmed to 20° C., stirred for 10 min, and cooled to 5° C. The mixture was added to a stirred solution of 1-oxide 13 (268 mg, 0.9 mmol) and trifluoroacetic acid (0.34 mL, 4.4 mmol) in DCM (20 mL) at 5° C. and the mixture stirred at 20° C. for 6 h. The solution was carefully diluted with dil. aq. NH$_3$ solution (2.0 mL) and the mixture extracted with CHCl$_3$ (5×50 mL). The organic fraction was dried and the solvent evaporated. The residue was purified by chromatography, eluting with a gradient (0-10%) of MeOH/DCM, to give 1,4-dioxide 14 (140 mg, 50%) as a red solid, mp (MeOH/DCM) 146-149° C.; $^1$H NMR δ 8.21 (d, J=9.6 Hz, 1 H, H-8), 7.52 (d, J=2.6 Hz, 1 H, H-5), 7.48 (br s, 1 H, NH), 7.10 (dd, J=9.6, 2.6 Hz, 1 H, H-7), 4.31-4.36 (m, 2 H, CH$_2$O), 3.81-3.84 (m, 2 H, CH$_2$O), 3.61-3.65 (m, 2 H, CH$_2$N), 3.47 (s, 3 H, OCH$_3$), 2.62 (br t, J=6.0 Hz, 2 H, CH$_2$N), 2.31 [s, 6 H, (CH$_3$)$_2$]; $^{13}$C NMR δ 165.2, 150.2, 140.2, 125.7, 123.5, 120.5, 95.6, 70.3, 68.8, 59.2, 57.5, 45.0 (2), 38.9. Anal. Calcd for C$_{14}$H$_{21}$N$_5$O$_4$¼CH$_2$Cl$_2$: C, 50.1; H, 6.2; N, 20.2. Found: C, 50.1; H, 6.1; N, 20.6%.

Example 5

N$^1$,N$^1$-Dimethyl-N$^2$-(6-ethoxy-1,4-dioxido-1,2,4-benzotriazin-3-yl)-1,2-ethanediamine (19)

5-Ethoxy-2-nitroaniline (15). A suspension of N-(5-ethoxy-2-nitrophenyl)acetamide (2.3 g, 10.3 mmol) in 5 M HCl (50 mL) was stirred at reflux temperature for 8 h. The resulting solution was cooled, diluted with water (200 mL), the resulting precipitate filtered and washed with water (2×10 mL) and dried to give aniline 15 (1.70 g, 90%) as an orange powder, mp (H$_2$O) 101-102° C.; $^1$H NMR δ 8.06 (d, J=9.5 Hz, 1 H, H-3), 6.27 (dd, J=9.5, 2.6 Hz, 1 H, H-4), 6.13 (d, J=2.6 Hz, 1 H, H-6), 5.80 (br s, 2 H, NH$_2$), 4.04 (q, J=7.0 Hz, 2 H, CH$_2$O), 1.42 (t, J=7.0 Hz, 3 H, CH$_3$); $^{13}$C NMR δ 164.8, 147.1, 128.4, 126.8, 106.9, 99.0, 64.1, 14.5. Anal. Calcd for C$_8$H$_{10}$N$_2$O$_3$: C, 52.7; H, 5.5; N, 15.4. Found: C, 52.6; H, 5.5; N, 15.4%.

6-Ethoxy-1,2,4-benzotriazin-3-amine 1-Oxide (16). A mixture of 5-ethoxy-2-nitroaniline (15) (1.63 g, 9.0 mmol) and cyanamide (1.50 g, 35.8 mmol) were mixed together at 100° C., cooled to 50° C., cHCl (15 mL) added carefully and the mixture heated at 100° C. for 4 h. The mixture was cooled to 50° C., 7.5 M NaOH solution added until the mixture was strongly basic and the mixture stirred at 100° C. for 3 h. The mixture was cooled, diluted with water (100 mL), filtered, washed with water (3×20 mL), washed with ether (3×5 mL) and dried. The residue was purified by chromatography, eluting with a gradient (0-10%) of MeOH/DCM, to give amine 16 (1.26 g, 68%) as a yellow powder, mp (MeOH) 268-271° C.; $^1$H NMR [(CD$_3$)$_2$SO] δ 8.02 (d, J=9.4 Hz, 1 H, H-8), 7.19 (brs, 2 H, NH$_2$), 6.92 (dd, J=9.4, 2.6 Hz, 1 H, H-7), 6.83 (d, J=2.6 Hz, 1 H, H-5), 4.17 (q, J=7.0 Hz, 2 H, CH$_2$O), 1.37 (t, J=7.0 Hz, 3 H, CH$_3$); $^{13}$C NMR [(CD$_3$)$_2$SO] δ 163.9, 160.7, 151.2, 124.8, 121.4, 117.1, 104.2, 64.2, 14.1. Anal. Calcd for C$_9$H$_{10}$N$_4$O2: C, 52.4; H, 4.9; N, 27.2. Found: C, 52.4; H, 4.8; N, 27.0%.

3-Chloro-6-ethoxy-1,2,4-benzotriazine 1-Oxide (17). Sodium nitrite (703 mg, 10.2 mmol) was added in small portions to a stirred solution of 1-oxide 16 (1.05 g, 5.1 mmol) in trifluoroacetic acid (30 mL) at 0° C. and the solution stirred at 20° C for 3 h. The solution was poured into ice/water, stirred 30 minutes, filtered, washed with water (3×30 mL) and dried. The solid was suspended in POCl$_3$ (30 mL) and DMF (0.5 mL) and stirred at 100° C. for 1 h. The solution was cooled, poured into ice/water, stirred for 30 minutes, filtered, washed with water (3×30 mL) and dried. The solid was suspended in DCM (150 mL), dried and the solvent evaporated. The residue was purified by chromatography, eluting with 5% EtOAc/DCM, to give chloride 17 (813 mg, 71%) as a pale yellow solid, mp (EtOAc/pet. ether) 150-153° C.; $^1$H NMR δ 8.28 (d, J=9.5 Hz, 1 H, H-8), 7.30 (dd, J=9.5, 2.6Hz, 1 H, H-7), 7.17 (d, J=2.6 Hz, 1 H, H-5), 4.22 (q, J=7.0 Hz, 2 H, CH$_2$O), 1.53 (t, J=7.0 Hz, 3 H, CH$_3$); $^{13}$C NMR δ 165.6, 157.7, 150.2, 128.8, 124.1, 121.8, 106.2, 65.2, 14.3. Anal. calcd for C$_9$H$_8$ClN$_3$O$_2$: C, 47.9; H, 3.6; N, 18.6; Cl, 15.7. Found: C, 48.2; H, 3.5; N, 18.7; Cl, 15.8%.

N$^1$-(6-Ethoxy-1-oxido-1,2,4-benzotriazin-3-yl)-N$^2$,N$^2$-dimethyl-1,2-ethanediamine (18). N,N-Dimethylethanediamine (0.48 mL, 4.4 mmol) was added to a stirred solution of chloride 17 (327 mg, 1.5 mmol) in DME (50 mL) and the solution stirred at reflux temperature for 2 h. The solution was cooled, the solvent evaporated and the residue partitioned between dilute aqueous NH$_3$ (100 mL) and DCM (100 mL). The organic fraction was dried and the solvent evaporated. The residue was purified by chromatography, eluting with a gradient (0-10%) MeOH/DCM, to give 1-oxide 18 (390 mg, 97%) as a yellow solid, mp (MeOH/EtOAc) 152-153° C.; $^1$H NMR δ 8.14 (d, J=9.4 Hz, 1 H, H-8), 6.85 (dd J=9.4, 2.6 Hz, 1 H, H-7), 6.82 (d, J=2.6 Hz, 1 H, H-5), 5.90 (br s, 1 H, NH), 4.14 (q, J=7.0 Hz, 2 H, CH$_2$O), 3.54 (br dd, J=5.8, 5.6 Hz, 2 H, CH$_2$N), 2.56 (br t, J=5.9 Hz, 2 H, CH$_2$N), 2.28 [s, 6 H, N(CH$_3$)$_2$], 1.48, (t, J=7.0 Hz, 3 H, CH$_3$); $^{13}$C NMR δ 164.8, 159.6, 151.5, 125.9, 122.0, 118.0, 104.4, 64.4, 57.5, 45.1 (2), 38.7, 14.5. Anal. Calcd for C$_{13}$H$_{19}$N$_5$O2¼H$_2$O: C, 55.4; H, 7.0; N, 24.9. Found: C, 55.6; H, 6.7; N, 25.2%.

N$^1$-(6-Ethoxy-1,4-dioxido-1,2,4-benzotriazin-3-yl)-N$^2$,N$^2$-dimethyl-1,2-ethanediamine (19). Hydrogen peroxide (70%, 0.7 mL, ca. 13.9 mmol) was added dropwise to a stirred solution of trifluoroacetic anhydride (2.0 mL, 13.9 mmol) in DCM (20 mL) at 5° C. The mixture was stirred at 5° C. for 5 min, warmed to 20° C., stirred for 10 min, and cooled to 5° C. The mixture was added to a stirred solution of 1-oxide 18 (385 mg, 1.4 mmol) and trifluoroacetic acid (0.53 mL, 6.9 mmol) in DCM (20 mL) at 5° C. and the mixture stirred at 20° C. for 6 h. The solution was carefully diluted with dil. aq. NH$_3$ solution (20 mL) and the mixture extracted with CHCl$_3$ (5×50 mL). The organic fraction was dried and the solvent evaporated. The residue was chromatographed, eluting with a gradient (0-10%) of MeOH/DCM, to give 1,4-dioxide 19 (125 mg, 31%) as a red solid, mp (MeOH/EtOAc) 150-152° C.; $^1$H NMR 8.23 (d, J=9.6 Hz, 1 H, H-8), 7.48 (d, J=2.6 Hz, 1 H, H-5), 7.46 (brs, 1 H, NH), 7.03 (dd, J=9.6, 2.6 Hz, 1 H, H-7), 4.25 (q, J=7.0 Hz, 2 H, CH$_2$O), 3.64 (br dd, J=6.0, 5.9 Hz, 2 H, CH$_2$N), 2.61 (t, J=6.0 Hz, 2 H, CH$_2$N), 2.30 [s, 6 H, (CH$_3$)$_2$], 1.49 (t, J=7.0 Hz, 3 H, CH$_3$); $^{13}$C NMR δ 165.5, 150.2, 140.3, 125.6, 123.5, 120.6, 95.4, 65.4, 57.5, 45.2 (2), 35.9, 14.3; MS (FAB$^+$) m/z 294 (MH$^+$, 100%), 278 (30), 276 (20); HRMS (FAB$^+$) calcd for C$_{13}$H$_{19}$N$_5$O$_3$ (MH$^+$) m/z 294.1566, found 294.1568. Anal. Calcd for C$_{13}$H$_{19}$N$_5$O$_3$: C, 53.2; H, 6.5; N, 23.9. Found: C, 53.1; H, 6.3; N, 23.6%.

Example 6

6-Ethyl-N-[3-(4-morpholinyl)propyl]-1,2,4-benzotriazin-3-amine 1,4-Dioxide (25)

5-Ethyl-2-nitroaniline (21). A mixture of 5-ethyl-2-nitroacetanilide (20) (1.90 g, 9.1 mmol) in 5 M HCl (80 mL) was heated at reflux temperature for 16 h. The resulting solution was cooled, diluted with water (100 mL), filtered, and dried to give nitroaniline 21 (1.47 g, 97%) as a brown oil, $^1$H NMR δ 8.02 (d, J=8.8 Hz, 1 H, H-3), 6.60 (d, J=1.8 Hz, 1 H, H-6), 6.54 (dd, J=8.8, 1.8 Hz, 1 H, H-4), 6.04 (m, 2 H, NH$_2$), 2.59 (q, J=7.6 Hz, 2 H, CH$_2$), 1.23 (t, J=7.6 Hz, 3 H, CH$_3$); $^{13}$C NMR δ 153.1, 144.8, 130.6, 126.2, 117.5, 117.0, 28.8, 14.5. Anal. calcd for C$_8$H$_{10}$N$_2$O$_2$: C, 57.8; H, 6.1; N, 16.9. Found: C, 58.0; H, 5.9; N, 17.1%.

6-Ethyl-1,2,4-benzotriazin-3-amine 1-Oxide (22). A mixture of 5-ethyl-2-nitroaniline (21) (1.38 g, 8.3 mmol) and cyanamide (1.40 g, 33.2 mmol) were mixed together at 100° C., cooled to 50° C., cHCl (15 mL) added carefully and the mixture heated at 100° C. for 4 h. The mixture was cooled to 50° C., 7.5 M NaOH solution added until the mixture was strongly basic and the mixture stirred at 100° C. for 3 h. The mixture was cooled, diluted with water (100 mL), filtered, washed with water (3×20 mL), washed with ether (3×5 mL) and dried. The residue was purified by chromatography, eluting with a gradient (0-10%) of MeOH/DCM, to give 1-oxide 22 (684 mg, 43%) as a yellow powder, mp (MeOH) 259-262° C.; $^1$H NMR [(CD$_3$)$_2$SO] δ 8.03 (d, J=8.8 Hz, 1 H, H-8), 7.31 (d, J=1.7 Hz, 1 H, H-5), 7.20-7.25 (m, 3 H, H-7, NH$_2$), 2.72 (q, J=7.6 Hz, 2 H, CH$_2$), 1.23 (t, J=7.6 Hz, 3 H, CH$_3$); $^{13}$C NMR [(CD$_3$)$_2$SO] δ 160.3, 152.4, 149.0, 128.2, 125.6, 123.2, 119.6, 28.2, 14.5. Anal. calcd for C$_9$H$_{10}$N$_4$O: C, 56.8; H, 5.3; N, 29.5. Found: C, 56.7; H, 5.1; N, 29.2%.

3-Chloro-6-ethyl-1,2,4-benzotriazine 1-Oxide (23). Sodium nitrite (477 mg, 3.9 mmol) was added in small portions to a stirred solution of 1-oxide 22 (657 mg, 3.5 mmol) in trifluoroacetic acid (20 mL) at 5° C. and the solution stirred at 20° C. for 3 h. The solution was poured into ice/water, stirred 30 minutes, filtered, washed with water (3×30 mL) and dried. The solid was suspended in POCl$_3$ (30 mL) and DMF (0.2 mL) and stirred at 100° C. for 1 h. The solution was cooled, poured into ice/water, stirred for 30 minutes, filtered, washed with water (3×30 mL) and dried. The solid was suspended in DCM (150 mL), dried and the solvent evaporated. The residue was purified by chromatography, eluting with 5% EtOAc/DCM, to give chloride 23 (428 g, 59%) as a pale yellow solid, mp (MeOH) 111-112° C.; $^1$H NMR δ 8.31 (d, J=8.9 Hz, 1 H, H-8), 7.76 (d, J=1.8 Hz, 1 H, H-5), 7.59 (dd, J=8.9, 1.8 Hz, 1 H, H-7), 2.90 (q, J=7.6 Hz, 2 H, CH$_2$), 1.36 (t, J=7.6 Hz, 3 H, CH$_3$); $^{13}$C NMR δ 157.0, 154.8, 147.7, 132.1, 132.0, 125.9, 120.0, 39.2, 14.1. Anal. Calcd for C$_9$H$_8$ClN$_3$O: C, 51.6; H, 3.9; N, 20.0; Cl, 16.9. Found: C, 51.8; H, 3.7; N, 20.1; Cl, 16.7%.

6-Ethyl-N-[3-(4-morpholinyl)propyl]-1,2,4-benzotriazin-3-amine 1-Oxide (24). 3-(1-morpholinyl)propylamine (0.63 mL, 4.3 mmol) was added to a stirred solution of chloride 23 (600 mg, 2.9 mmol) and Et$_3$N (0.80 mL, 5.7 mmol) in DME (50 mL) and the solution stirred at reflux temperature for 12 h. The solution was cooled, the solvent evaporated and the residue partitioned between dilute aqueous NH$_3$ (100 mL) and DCM (100 mL). The organic fraction was dried and the solvent evaporated. The residue was purified by chromatography, eluting with a gradient (0-10%) of MeOH/DCM, to give 1-oxide 24 (840 mg, 93%) as a yellow powder, mp (MeOH/DCM) 123-124° C.; $^1$H NMR δ 8.16 (d, J=8.8 Hz, 1 H, H-8), 7.38 (brs, 1 H, H-5), 7.12 (dd, J=8.8, 1.8 Hz, 1 H, H-7), 6.29 (brs, 1 H, NH), 3.73-3.77 (m, 4 H, 2×CH$_2$O), 3.57-3.63 (m, 2 H, CH$_2$N), 2.76 (q, J=7.6 Hz, 2 H, CH$_2$), 2.45-2.53 (m, 6 H, 3×CH$_2$N), 1.81-1.88 (m, 2 H, CH$_2$) 1.31 (t, J=7.6 Hz, 3 H, CH$_3$); $^{13}$C NMR δ 159.2, 152.9, 149.2, 129.3, 126.0, 124.0, 120.3, 67.0 (2), 57.3, 53.8 (2), 40.9, 29.1, 25.2, 14.6. Anal. Calcd for C$_{16}$H$_{23}$N$_5$O$_2$: C, 60.6; H, 7.3; N, 22.1. Found: C, 60.6;H, 7.2; N, 22.1%.

6-Ethyl-N-[3-(4-morpholinyl)propyl]-1,2,4-benzotriazin-3-amine 1,4-Dioxide (25). Oxidation of 1-oxide 24 (829 mg, 2.6 mmol) with CF$_3$CO$_3$H (ca. 26.1 mmol) gave (i) starting material 24 (270 mg, 32%) and (ii) 1,4-dioxide 25 (206 mg, 24%) as a red solid, mp (MeOH/EtOAc) 142-144° C.; $^1$H NMR δ 8.55 (br s, 1 H, NH), 8.22 (d, J=9.0 Hz, 1 H, H-8), 8.10 (d, J=1.7 Hz, 1 H, H-5), 7.31 (dd, J=9.0, 1.7 Hz, 1 H, H-7), 3.82-3.87 (m, 4 H, 2×CH$_2$O), 3.66-3.72 (m, 2 H, CH$_2$N), 2.86 (q, J=7.6 Hz, 2 H, CH$_2$), 2.58 (br dd, J=6.2, 6.0 Hz, 2 H, CH$_2$N), 2.49-2.55 (m, 4 H, 2×CH$_2$N), 1.85-1.92 (m, 2 H, CH$_2$), 1.35 (t, J=7.6 Hz, 3 H, CH$_3$); $^{13}$C NMR δ 153.9, 150.0, 138.5, 128.8, 128.2, 121.5, 114.9, 66.9 (2), 57.8, 53.9 (2), 41.7, 29.5, 24.4, 14.5. Anal. Calcd for C$_{15}$H$_{23}$N$_5$O$_3$: C, 57.6; H, 7.0; N, 21.0. Found: C, 57.6; H, 6.9; N, 20.9%

Example 7

2-[(3-Ethyl-1,4-dioxido-1,2,4-benzotriazin-6-yl) oxy]-N, N-dimethylethaneamine (30)

3-Chloro-6-fluoro-1,2,4-benzotriazine 1-Oxide (27). Sodium nitrite (2.94 g, 42.6 mmol) was added in small portions to a stirred solution of amine 26 [Hay et. al., J. Med. Chem. 2003, 46, 169] (3.84 g, 21.3 mmol) in trifluoroacetic acid (80 mL) at 5° C. and the solution stirred at 20° C. for 3 h. The solution was poured into ice/water, stirred 30 minutes, filtered, washed with water (3×30 mL) and dried. The solid was suspended in POCl$_3$ (80 mL) and DMF (0.5 mL) and stirred at 100° C. for 1 h. The solution was cooled, poured into ice/water, stirred for 30 minutes, filtered, washed with water (3×30 mL) and dried. The solid was suspended in DCM (150 mL), dried and the solvent evaporated. The residue was purified by chromatography, eluting with 5% EtOAc/DCM, to give chloride 27 (1.91 g, 45%) as a pale yellow solid, mp (EtOAc) 166-168° C.; $^1$H NMR δ 8.45 (dd, J=9.5, 5.3 Hz, 1 H, H-8), 7.61 (dd, J=2.6 Hz, 1 H, H-5), 7.47-7.52 (m, 1 H, H-7); $^{13}$C NMR δ 167.1 (q, J=264 Hz), 158.4, 149.2, 131.0, 123.4 (d, J=11 Hz), 120.1 (d, J=26 Hz), 112.9 (d, J=23 Hz). Anal. Calcd for C$_7$H$_3$ClFN$_3$O: C, 42.1; H, 1.5; N, 21.1; Cl, 17.8. Found: C, 42.4; H, 1.6; N, 21.2; Cl, 17.8%.

3-Ethyl-6-fluoro-1,2,4-benzotriazine 1-Oxide (28). Pd(PPh$_3$)$_4$ (196 mg, 0.17 mmol) was added to a stirred solution of chloride 27 (329 mg, 1.7 mmol) and tetraethyltin (0.7 mL, 3.3 mmol) in DME (20 mL), the solution degassed, and stirred under N$_2$ at reflux temperature for 16 h. The solvent was evaporated and the residue purified by chromatography, eluting with 20% EtOAc/pet. ether to give an oil which was further purified by chromatography, eluting with 5% EtOAc/DCM, to give 1-oxide 28 (295 mg, 93%) as a white solid, mp (EtOAc/pet. ether) 122-124° C.; $^1$H NMR δ 8.48 (dd, J=9.5, 5.5 Hz, 1 H, H-8), 7.60 (dd, J=8.7, 2.6 Hz, 1 H, H-5), 7.38 (m, 1 H, H-7), 3.04 (q, J=7.6 Hz, 2 H, CH$_2$), 1.43 (t, J=7.6 Hz, 3 H, CH$_3$); $^{13}$C NMR δ 168.6 (q, J=175 Hz), 165.1, 149.5(d, J=15 Hz), 130.5, 123.2 (d, J=11 Hz), 120.0 (d, J=26 Hz), 112.7 (d, J=22 Hz), 30.7, 12.2. Anal. Calcd for C$_9$H$_8$FN$_3$O: C, 56.0; H, 4.2; N, 21.8. Found: C, 56.0; H, 4.2; N, 21.8%.

2-[(3-Ethyl-1-oxido-1,2,4-benzotriazin-6-yl)oxy]-N,N-dimethylethaneamine (29). Sodium (54 mg, 2.33 mmol) was added to a stirred solution of fluoride 28 (300 mg, 1.55 mmol) in N,N-dimethylethanolamine (8 mL) and the solution stirred at 20° C. for 2.5 h under N$_2$. Water was added and the mixture extracted with DCM (4×20 mL), the combined organic fraction dried and the solvent evaporated. The residue was purified by column chromatography, eluting with a gradient (0-5%) MeOH/DCM to give 1-oxide 29 (24d mg, 59%) as a pale yellow powder, mp 80-82° C.; $^1$H NMR δ 8.33 (d, J=9.5 Hz, 1 H, H-8), 7.29 (dd, J=9.5, 2.6 Hz, 1 H, H-7), 7.20 (d, J=2.6 Hz, 1-H, H-5), 4.23 (t, J=5.6 Hz, 2 H, OCH$_2$), 3.00 (q, J=7.6 Hz, 2 H, CH$_2$), 2.82 (t, J=5.6 Hz, 2 H, NCH$_2$), 2.37 [s, 6 H, N(CH$_3$)$_2$], 1.43 (t, J=7.6 Hz, 3 H, CH$_3$); $^{13}$C δ 168.8, 164.5, 150.3, 128.5, 123.2, 121.6, 106.3, 67.2, 57.8, 45.9 (2), 30.7, 12.2. Anal. Calcd for C$_{13}$H$_{18}$N$_4$O$_2$: C, 59.5; H, 6.9; N, 21.4. Found: C, 59.3; H, 6.7; N, 21.6%.

2-[(3-Ethyl-1,4-dioxido-1,2,4-benzotriazin-6-yl)oxy]-N, N-dimethylethaneamine (30). Hydrogen peroxide (70%; 0.30 mL, ca. 6.1 mmol) was added dropwise to a stirred solution of trifluoroacetic anhydride (0.85 mL, 6.1 mmol) in DCM (15 mL) at 5° C. The solution was stirred at 20° C. for 10 min, then cooled to 5° C., added to a solution of 1-oxide 29 (160 mg, 0.61 mmol) and trifluoroactic acid (0.10 mL, 1.31 mmol) in DCM (15 mL) at 5° C. The solution was stirred at 20° C. for 16 h, diluted with dilute aqueous NH$_3$ solution (40 mL) and extracted with CHCl$_3$ (4×40 mL). The combined organic fraction was dried (Na$_2$SO$_4$) and the solvent evaporated. The residue was purified by column chromatography, eluting with a gradient (0-8%) MeOH/CH$_2$Cl$_2$ to give 1,4-dioxide 30 (55 mg, 32%) as a bright yellow solid, mp (MeOH, EtOAc) 146-149° C.; $^1$H NMR δ 8.33 (d, J=9.6 Hz, 1 H, H-8), 7.78 (d, J=2.6 Hz, 1 H, H-5), 7.42 (dd, J=9.6, 2.6 Hz, 1 H, H-7), 4.30 (t, J=5.4 Hz, 2 H, OCH$_2$), 3.21 (q, J=7.5 Hz, 2 H, CH$_2$), 2.83 (t, J=5.4 Hz, 2 H, NCH$_2$), 2.37 [s, 6 H N(CH$_3$)$_2$], 1.43 (t, J=7.4 Hz, 3 H, CH$_3$); $^{13}$C δ 164.9, 157.1, 141.5, 129.7, 124.7, 123.4, 98.0, 67.9, 57.7, 45.8 (2), 24.1, 9.3. Anal. Calcd for C$_{13}$H$_{18}$N$_4$O$_3$.¼MeOH: C, 55.6; H, 6.7; N, 19.6. Found: C, 55.5; H, 6.4; N, 19.5%.

Example 8

3-Ethyl-6-[3-(4-morpholinyl)propoxy]-1,2,4-benzotriazine 1,4-Dioxide (32)

3-Ethyl-6-[3-(4-morpholinyl)propoxy]-1,2,4-benzotriazine 1-Oxide (31). NaH (60% dispersion in oil, 310 mg, 7.75 mmol) was added to dry THF (10 mL) and stirred at 20° C. for 20 min prior to the addition of 3-(4-morpholinyl)propanol (676 mg, 4.66 mmol). The mixture was stirred for 30 min, fluoride 28 (300 mg, 1.55 mmol) added and the resulting solution stirred at 20° C. for 2.5 h under $N_2$. Water was added and the solution extracted with DCM (4×30 mL). The combined organic fraction was dried and the solvent evaporated. The residue was purified by column chromatography, eluting with a gradient (0-5%) MeOH/DCM to give 1-oxide 31 (257 mg, 52%) as a pale yellow solid, mp 108-111° C.; $^1$H NMR δ 8.33 (d, J=9.3 Hz, 1 H, H-8), 7.21-7.26 (m, 2 H, H-7 and H-5), 4.22 (t, J=6.4 Hz, 2 H, $CH_2$), 3.73 (t, J=4.6 Hz, 4 H, 2×$CH_2$O), 3.00 (q, J=7.6 Hz, 2 H, $CH_2$), 2.55 (t, J=7.0 Hz, 2 H, $CH_2$), 2.48 (t, J=4.6 Hz, 4 H, 2×$CH_2$N), 2.06 (m, 2 H, $CH_2$), 1.43 (t, J=7.6 Hz, 3 H, $CH_3$); $^{13}$C NMR δ 168.7, 164.6, 150.3, 128.4, 123.1, 121.6, 106.3, 67.3 (2), 66.9, 55.1, 53.7 (2), 30.7, 26.0, 12.2. Anal. Calcd for $C_{16}H_{22}N_4O_3$: C, 60.4; H, 7.0; N, 17.6. Found: C, 60.4; H, 7.0; N, 17.4%.

3-Ethyl-6-[3-(4-morpholinyl)propoxy]-1,2,4-benzotriazine 1,4-Dioxide (32). Hydrogen peroxide (70%; 0.53 mL, ca. 10.43 mmol) was added dropwise to a stirred solution of trifluoroacetic anhydride (1.45 mL, 10.43 mmol) in DCM (20 mL) at 5° C. The solution was stirred at 20° C. for 10 min, then cooled to 5° C., added to a solution of 1-oxide 31 (260 mg, 1.04 mmol) and trifluoroactic acid (0.17 mL, 2.23 mmol) in $CHCl_3$ (20 mL) at 5° C. The solution was stirred at 20° C. for 24 h, diluted with dilute aqueous $NH_3$ solution (50 mL) and extracted with $CHCl_3$ (4×50 mL). The combined organic fraction was dried and the solvent evaporated. The residue was purified by column chromatography, eluting with 5% MeOH/DCM to give 1,4-dioxide 32 (90 mg, 32%) as a bright yellow solid, mp 123-126° C.; $^1$H NMR δ 8.36 (d, J=9.5 Hz, 1 H, H-8), 7.77 (d, J=2.6 Hz, 1 H, H-5), 7.36 (dd, J=9.5, 2.6 Hz, 1 H, H-7), 4.29 (t, J=6.4 Hz, 2 H, $CH_2$), 3.72 (t, J=4.6 Hz, 4 H, 2×$CH_2$O), 3.21 (q, J=7.5 Hz, 2 H, $CH_2$), 2.54 (t, J=7.0 Hz, 2 H, $CH_2$), 2.47 (t, J=4.6 Hz, 4 H, 2×$CH_2$N), 2.10-2.04 (m, 2 H, $CH_2$), 1.44 (t, J=7.5 Hz, 3 H, $CH_3$); $^{13}$C NMR δ 165.1, 157.1, 141.5, 129.6, 124.4, 123.4, 98.0, 68.1, 66.9 (2), 55.0, 53.7 (2), 25.9, 24.1, 9.3. Anal. Calcd for $C_{16}H_{22}N_4O_4$: C, 57.5; H, 6.3; N, 16.8. Found: C, 57.2; H, 6.5; N, 16.5%.

Example 9

6-Methyl-1,2,4-benzotriazin-3-amine 1,4-Dioxide (33)

Compound 33 was prepared as previously described (Hay et. al., *J. Med. Chem.* 2003, 46,169).

Example 10

7-Chloro-1,2,4-benzotriazin-3-amine 1,4-Dioxide (34)

Compound 34 was prepared as previously described (Hay et. al., *J. Med. Chem.* 2003, 46, 169).

Example 11

8-Chloro-1,2,4-benzotriazin-3-amine 1,4-Dioxide (34)

Compound 35 was prepared as previously described (Hay et. al., *J. Med. Chem.* 2003, 46, 169).

Example 12

7-(Methylsulfonyl)-1,2,4-benzotriazin-3-amine 1,4-Dioxide (36)

Compound 36 was prepared as previously described (Hay et. al., *J. Med. Chem.* 2003, 46, 169).

Example 13

7-Methyl-N-[2-(dimethylamino)ethyl]-1,2,4-benzotriazin-3-amine 1,4-Dioxide (40)

3-Chloro-7-methyl-1,2,4-benzotriazine 1-Oxide (38). A solution of $NaNO_2$ (3.9 g, 56.3 mmol) in water (15 mL) was added dropwise to a stirred suspension of amine 37 (4.95 g, 28.1 mmol) in 2 M HCl (200 mL) at 5° C. and the mixture stirred vigorously for 2 h at 20° C. The suspension was filtered, the solid dissolved in dil. aq. $NH_3$ (150 mL), filtered and the filtrate acidified with cHCl. The suspension was cooled, filtered and the solid washed with water (2×10 mL) and dried. The solid (3.76 g, 21.2 mmol) was suspended in dimethylaniline (6.7 mL, 53 mmol) and POCl3 (14 mL, 149 mmol). The mixture was stirred at reflux temperature for 1 h, the resulting solution poured on to ice (300 mL). The suspension was filtered, washed with water (2×20 mL), dissolved in EtOAc (200 mL), dried and the solvent evaporated. The residue was chromatographed, eluting with 5% EtOAc/DCM, to give chloride 38 (2.99 g, 72%) as a yellow solid, mp 176.5-177° C. [lit. (W. O. Foye et. al., *J. Het. Chem.* 1982, 19, 497) (toluene) 177-179° C.]; $^1$H NMR δ 8.21 (d, J=2.0 Hz, 1 H, H-8), 7.89 (d, J=8.6 Hz, 1 H, H-5), 7.81 (dd, J=8.6, 2.0 Hz, 1 H, H-6), 2.61 (s, 3 H, $CH_3$).

7-Methyl-N-[2-(dimethylamino)ethyl]-1,2,4-benzotriazin-3-amine 1-Oxide (39). 2-(Dimethylamino) (1.0 mL, 9.0 mmol) was added to a stirred solution of chloride 38 (700 mg, 3.6 mmol) in DME (50 mL) and the solution stirred at reflux temperature for 8 h. The solution was cooled, the solvent evaporated and the residue partitioned between dil. aq. $NH_3$ (100 mL) and DCM (100 mL). The organic fraction was dried and the solvent evaporated. The residue was purified by chromatography, eluting with a gradient (0-10%) MeOH/DCM, to give 1-oxide 39 (781 mg, 88%) as a yellow solid, mp (DCM) 143-144° C.; $^1$H NMR [$(CD_3)_2$SO] δ 7.93 (br s, 1 H, H-8), 7.60-7.64 (m, 2 H, NH, H-6), 7.48 (d, J=8.6 Hz, 1 H, H-5), 3.37-3.45 (m, 2 H, $CH_2$N), 2.46-2.52 (m, 2 H, $CH_2$N), 2.41 (s, 3 H, $CH_3$), 2.21 [s, 6 H, N($CH_3$)$_2$]; $^{13}$C NMR [$(CD_3)_2$SO] δ 158.6, 146.8, 137.6, 134.6, 129.6, 125.8, 118.4, 57.6, 45.1 (2), 39.0, 20.6. Anal. Calcd for $C_{12}H_{17}N_5O$: C, 58.3; H, 6.9; N, 28.3. Found: C, 58.5: H, 7.2; N, 28.6%.

7-Methyl-N-[2-(dimethylamino)ethyl]-1,2,4-benzotriazin-3-amine 1,4-Dioxide (40). Hydrogen peroxide (70%, 1.0 mL, ca. 20.6 mmol) was added dropwise to a stirred solution of trifluoroacetic anhydride (2.9 mL, 20.6 mmol) in DCM (8 mL) at 5° C. The mixture was stirred at 5° C. for 5 min, warmed to 20° C., stirred for 10 min, and cooled to 5° C. The mixture was added to a stirred solution of 1-oxide 39 (510 mg, 2.1 mmol) and TFA (238 μL, 3.1 mmol) in $CHCl_3$ at 5° C. and the mixture stirred at 20° C. for 16 h. The solution was carefully diluted with aq. $KHCO_3$ solution (20 mL) and the mixture extracted with $CHCl_3$ (5×50 mL). The organic fraction was dried and the solvent evaporated. The residue was purified by chromatography, eluting with a gradient (0-10%) of MeOH/DCM, followed by 1% $Et_3$N/10% MeOH/DCM, to give (i) starting material 39 (98 mg, 19%) spectroscopically identical with sample prepared above; and (ii) 1,4-dioxide 40 (193 mg, 35%) as a red solid, which was dissolved in HCl saturated MeOH, the solvent evaporated and the residue crystallized to give the hydrochloride, mp (MeOH/EtOAc) 180-182° C.; $^1$H NMR [$(CD_3)_2$SO] δ 10.66 (br s, 1 H, $NH^+Cl^-$), 8.80 (t, J=5.6 Hz, 1 H, NH), 8.08 (d, J=1.5 Hz, 1 H, H-8), 8.03 (d, J=8.8 Hz, 1 H, H-5), 7.88 (dd, J=8.8, 1.5 Hz, 1 H, H-6), 3.77-3.83 (m, 2 H, $CH_2$N), 3.33-3.38 (m, 2 H, $CH_2$N), 2.82 [d, J=4.8 Hz, 6 H, N($CH_3$)$_2$]; $^{13}$C NMR [$(CD_3)_2$SO] δ 149.4, 138.2, 138.0, 136.3, 130.3, 119.6, 116.4, 54.9, 42.3 (2), 36.0, 20.7. Anal. Calcd for $C_{12}H_{18}H_5O_2 \cdot 2HCl \cdot 1/4H_2O$: C, 42.3; H, 5.8; N, 20.6. Found: C, 42.3: H, 5.9; N, 20.8%.

Example 14

HT29 Excision Assay

Compounds were evaluated with single dose radiation using s.c. HT29 tumors (average of two largest diameters 7-10 mm) grown by inoculating $10^7$ cells (obtained by enzymatic dissociation of multicellular spheroids). Drugs were administered as single i.p. doses at their MTD with the following groups in each experiment. A: vehicle control, B: test drug, C: Radiation (20 Gy, cobalt-60, whole body irradiation), D: TPZ (316 µmol/kg) 5 min after radiation, E: Test drug 5 min after radiation. Each group included 3 (A, B) or 5 (C-E) mice. Tumors were excised 18 hr after treatment and plated to determine clonogenicity. Hypoxic cytotoxicity is determined by the difference in surviving fraction between groups C and E, while comparison of A and B evaluates oxic cell killing. Total yield of clonogens was used as the key parameter if cell yields were affected by treatment. Results of this assay are illustrated for compound 3 (and TPZ) in FIG. 5. Compound 3 is predicted to be active because it meets all the desired characteristics of a TPZ analogue of this invention (see Table 2), and is demonstrated to have significant activity against hypoxic (radioresistant) cells in HT29 cells (p<0.01 relative to radiation only).

Wherein the foregoing description reference has been made to reagents, or integers having known equivalents thereof, then those equivalents are herein incorporated as if individually set forth.

While this invention has been described with reference to certain embodiments and examples, it is to be appreciated that further modifications and variations can be made to embodiments and examples without departing from the scope of the invention.

The invention claimed is:

1. A compound selected from 3-ethyl-6-[3-(4-morpholinyl)propoxy]-1,2,4-benzotriazine 1,4-dioxide and pharmacologically acceptable salts thereof.

2. A method of treating a cancer selected from cervical carcinoma, colon carcinoma and non-small cell lung cancer, comprising the steps of (1) administering a compound as claimed in claim 1 in a therapeutically effective amount to tumour cells in a subject, wherein the tumour cells are in a hypoxic environment, and (2) administering radiotherapy to the tumour cells before, during or after the administration of the compound as defined in claim 1 to the tumour cells.

3. The method as claimed in claim 2 further including the step of administering one or more chemotherapeutic agents to the tumour cells before, during or after the administration of the compound as defined in claim 1 to the tumour cells.

4. The method as claimed in claim 3 wherein the one or more chemotherapeutic agents is selected from Cisplatin or other platinum-based derivatives, Temozolomide or other DNA methylating agents, cyclophosphamide or other DNA alkylating agents, Doxorubicin, mitoxantrone, camptothecin or other topoisomerase inhibitors, Methotrexate, gemcitabine and/or Docetaxel or other taxanes.

5. A method of radiosensitising in a subject tumour cells of solid tumours selected from the group consisting of cervical carcinoma, colon carcinoma and non-small cell lung cancer in hypoxic conditions in vivo, comprising the steps of:
(a) administering to the subject a pharmaceutical composition in an amount sufficient to produce radiosensitivity in the tumour cells, the composition comprising a compound as claimed in claim 1; and
(b) subjecting the tumour cells to radiation.

6. A pharmaceutical composition comprising a therapeutically effective amount of a compound as defined in claim 1 and a pharmaceutically acceptable excipient, adjuvant, carrier, buffer or stabiliser.

* * * * *

UNITED STATES PATENT AND TRADEMARK OFFICE
CERTIFICATE OF CORRECTION

PATENT NO. : 7,816,521 B2
APPLICATION NO. : 10/590796
DATED : October 19, 2010
INVENTOR(S) : Denny et al.

Page 1 of 1

It is certified that error appears in the above-identified patent and that said Letters Patent is hereby corrected as shown below:

Column 1, lines 5-8, please delete, "The invention described herein was made in the course of work under grant or contract from the United States Department of Health and Human Services. The United States Government has certain rights to this invention", please insert as follows: -- This invention was made with government support under grand number PO1 CA 082566, awarded by National Institutes of Health (NIH). The government has certain rights in the invention. --.

Signed and Sealed this
Twenty-fourth Day of May, 2011

David J. Kappos
*Director of the United States Patent and Trademark Office*